United States Patent [19]

Asato et al.

[11] Patent Number: 5,235,076
[45] Date of Patent: Aug. 10, 1993

[54] AZULENIC RETINOID COMPOUNDS, COMPOSITIONS AND METHODS

[75] Inventors: Alfred E. Asato, Waipahu; Robert S. H. Liu, Honolulu, both of Hi.

[73] Assignee: University of Hawaii, Honolulu, Hi.

[21] Appl. No.: 706,950

[22] Filed: May 28, 1991

[51] Int. Cl.[5] .......................................... C07C 231/00
[52] U.S. Cl. ..................................... 554/35; 554/221; 560/128; 562/510; 568/445; 568/823; 568/828
[58] Field of Search ................... 260/410; 554/221, 35; 560/128; 562/510; 568/445, 823, 828; 514/558, 659, 661, 693, 703, 763, 766, 859

[56] References Cited

U.S. PATENT DOCUMENTS

| | | | |
|---|---|---|---|
| 4,310,546 | 1/1982 | Gander | 424/311 |
| 4,565,863 | 1/1986 | Ballag et al. | 536/18.2 |
| 4,568,757 | 2/1986 | Carroll et al. | 549/294 |
| 4,727,088 | 2/1988 | Scott et al. | 514/725 |
| 4,826,871 | 5/1989 | Gressel et al. | 514/438 |
| 4,885,311 | 12/1989 | Parish et al. | 514/549 |
| 4,902,604 | 2/1990 | Yamaguchi et al. | 430/281 |
| 4,904,566 | 2/1990 | Schrott et al. | 430/270 |
| 4,912,134 | 3/1990 | Yasunami et al. | 514/510 |

FOREIGN PATENT DOCUMENTS

| | | |
|---|---|---|
| 338426 | 10/1989 | European Pat. Off. . |
| 63-30430 | 2/1988 | Japan . |
| WO88/00191 | 1/1988 | PCT Int'l Appl. . |
| 83134 | 2/1984 | Romania . |

OTHER PUBLICATIONS

Chemical Abstracts, vol. 99, No. 11, 1983, p. 589 88414r.
Chemical Abstracts, vol. 102, p. 315, 100823p.
Chemical Abstracts, vol. 102, #12, p. 315, 100823p, 1985.
Asato et al, Journal of the American Chemical Society, vol. 112, #20, pp. 7398-7399, 1990.
Horino et al, Bulletin of the Chemical Society of Japan vol. 64, #1, 1991, pp. 183-190.
Zarilli, G. R., "synthesis of retinal analogs for biological and bioorganic studies: Chlamydomonas, a new model for photoreceptor studies," Ph.D. thesis submitted to Columbia University, 1984, pp. 48-88 and 132-142.
Liu, R. S. H. and A. E. Asato, *Methods Enzymol.* 88:506 (1982).
Nakanishi, et al., Pure Appl. Chem. 61:361 (1989).
Foster, et al., Biochem. 28:819 (1989).
Derguini, et al., Pure Appl. Chem. 58:719 (1986).
Derguini, et al., J. Am. Chem. Soc. 105:646 (1983).
Lugtenburg, et al., J. Am. Chem. Soc. 108:3104 (1986).
Sandorfy, C. and Vocelle, D., Can. J. Chem. 64:2251 (1986).
Mead, et al., Tetrahedron Lett. 28:259 (1987).
Tierno, et al., Biochem. 29:5948 (1990).
Jaffer, H. H.; Orchin, M., Theory and Applications of Ultraviolet Spectroscopy; John Wiley & Sons, Inc.: New York, 1962; pp. 337–341.
Foster et al., "Activation of Chlamydonas Rhodospin in Viro Does Not Require Isomerization of Retinal". Biochemistry 28:819-824, esp. p. 821 (1989).
Nakanishi et al., "Theory of rhodopsin activation: probable charge redistribution of excited state chromophore." Pure & Applied Chemistry 61, No. 3:361-362 (1989).
Asato et al., "Azulenic Retinoids and the Corresponding Bacteriorhodopsin Analogues. Usually Red-Shifted Pigments." J. Am. Chem. Soc. 112:7398-7399 (1989).
Suciu et al., "RO, A, 83,134". Chem Abstract 102, No. 12:315, 100823 (1984).

*Primary Examiner*—José G. Dees
*Assistant Examiner*—D. Carr
*Attorney, Agent, or Firm*—James C. Weseman

[57] ABSTRACT

Novel azulenic retinoid compounds and therapeutic compositions are disclosed, along with method for their production and use as anti-cancer and cancer-prevention agents. The compositions of the present invention will also find use in treating dermatological disorders such as acne and psoriasis, as well as dermatologically-related conditions such as repair and effacement of wrinkles.

10 Claims, 13 Drawing Sheets a = (EtO)$_2$P(O)CH$_2$CN, LDA, THF
b = DIBAL
c = (EtO)$_2$P(O)CH$_2$C(CH$_3$)=CHCN, LDA, THF
d = (EtO)$_2$P(O)CH$_2$C(CH$_3$)=CFCO$_2$Et, LDA, THF
e = MnO$_2$
f = CF$_3$COCH$_3$, piperidine, HOAc

AZULENIC RETINOID COMPOUNDS, COMPOSITIONS AND METHODS

DESCRIPTION

Technical Field

The present invention relates generally to compounds, therapeutic compositions and methods for preventing and treating cancers and various dermatological disorders, and more specifically to useful azulenic retinoid compounds, therapeutic compositions and methods for their production and use.

BACKGROUND OF THE INVENTION

Retinol (vitamin A) and retinoic acid (vitamin A acid), their isomers, and certain of their analogues are known to play an essential role in controlling the normal differentiation of epithelial tissues and have therefore found use in controlling premalignant epithelial cell differentiation, as well as displaying beneficial effects in the treatment of acne and keratinizing skin disorders. However, a number of side effects complicate the administration of large doses of vitamin A. Hypervitaminosis A can be manifested as weight loss, desquamation of the skin, hair loss, irritation of the oral and pharyngeal mucosa, nose bleeds, headaches, bone pain, liver toxicity due to storage of vitamin A in the liver, papilledema, pseudotumor cerebri, demineralization and periosteal thickening of the bones. These difficulties, as well as the known toxicity of vitamin A and its analogues at high dosage level render these natural retinal compounds as well as their esters, acetates and palmitates undesirable for treatment of neoplastic or dermatopathic conditions.

Azulenic compounds are also known to have beneficial effects as anti-inflammatory, anti-dermatopathic, anti-allergenic, anti-tumorigenic and immunomodulatory agents, in addition to having applications in non-biological areas.

There is an on-going need for compounds, therapeutic compositions and methods for preventing and treating cancers and various dermatological disorders, which do not display the undesirable and toxic side-effects of vitamin A and related compounds.

DESCRIPTION OF THE PRIOR ART

Compounds sharing certain structural attributes with those of the present invention have previously been described, without an indication of therapeutic biological activity. For example, Jutz, C. "Vinylogs of azulene-1-carboxaldehydes and their condensation with azulenes," German Patent 1,079,692 (Apr. 14, 1960) discloses compounds including: 3-(I-azulenyl)-2-propenal, 3-(1,4-dimethyl-7-isopropyl-3-azulenyl)-2-propenal, 5-(1,4-dimethyl-7-isopropyl-3-azulenyl)-2,4-pentadienal and 5-(1-azulenyl)-2,4-pentadienal.

In addition, certain azulene-containing bacteriorhodopsin analogues are known, with the retinoid side chain originating from the 2'-position (Zarilli, G. R., "Synthesis of retinal analogs for biological and bioorganic studies: Chlamydomonas, a new model for photoreceptor studies," Ph.D. thesis submitted to Columbia University, 1984).

DISCLOSURE OF THE INVENTION

The present invention provides azulenic retinoid compounds, therapeutic compositions containing such compounds, and methods for their production and use as anti-neoplasm and anti-dermatopathic agents for preventing and treating cancers and various dermatological disorders.

In the practice of the instant invention, there is provided at least one azulenic retinoid having the general structure of a compound in accordance with the formula:

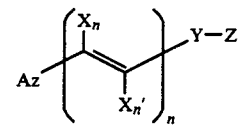

Wherein
n is an integer from 1 to 4;
each $X_n$ or $X_n'$ group can independently be taken to be H, alkyl, F, Cl or $CF_3$;
Az is an azulenic substituent group of the following general formula:

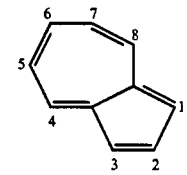

wherein
the azulenic group can be attached via any of carbons 1 to 8 to the unsaturated retinoid backbone, and
the azulene group can be further modified by additional alkyl substituents at any one or more of the remaining carbons;
the Y group can be $C_{1-10}$ straight or branched chain alkyl or an aromatic functional group of the following formula:

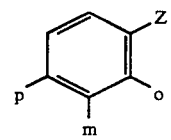

wherein the Y group can be bonded to the unsaturated retinoid backbone at either the para- (p), meta- (m), or ortho- (o)-position of the benzene ring, or can be des-Y; and
the Z group can be any polar end group such as aldehyde (CHO), alcohol ($CH_2OH$), acetate ($CH_2O\text{-}COCH_3$), or carboxylic acid ($CO_2H$) and its derivatives such as esters ($CO_2R$) and amides ($CONRR'$);
with the provisos that:
when the Az group is azulene attached to the unsaturated retinoid backbone via the 1' carbon or guaiazulene attached to the unsaturated retinoid backbone via the 3' carbon, and n=1 or 2, then at least one of the following limitations apply:
at least one $X_n$ or $X_n'$ group is not H;
Y is not des-Y; or
z is not CHO;
when the Az group is azulene attached to the unsaturated retinoid backbone via the 2' carbon, then at least one of the following limitations apply:

when n=1, then either $X_1$ is not $CH_3$ or Y is not des-Y, or Z is not CHO; or when n=3, then either $X_3$ is not $CH_3$ or Y is not des-Y, or Z is not CHO or $COOCH_3CH_3OH$;

Typically, representative azulenic retinoid compounds employed in the practice of the invention comprise a central $C_{2-8}$ isoprene moiety to form a retinoid backbone, an azulenic or guaiazulenic group attached to the n'-end of the retinoid backbone and at least one methyl group independently substituted at the X or X' positions on the backbone.

Also provided in accordance with aspects of the invention are pharmaceutical compositions useful as anti-cancer and cancer-prevention agents, anti-dermatopathic agents and/or immunomodulators, which compositions contain the above-recited azulenic retinoid compounds together with a pharmaceutically acceptable carrier. Administration of therapeutically effective doses of these compositions can provide effective delivery of the above-recited biological activities to mammalian hosts.

Additional aspects of the present invention provide methods for producing such useful compounds and compositions, and methods for using the compounds and compositions as therapeutic agents.

BRIEF DESCRIPTION OF THE DRAWINGS

FIGS. 3 through 13 are diagrammatic representations of synthetic protocols for selected azulenic retinoid compounds of the invention.

DETAILED DESCRIPTION OF THE INVENTION

Figure 1:
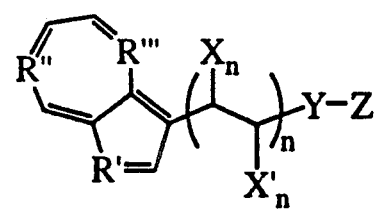
FIG. 1 is a diagrammatic representation of the generalized structure of azulenic retinoid compounds disclosed in the present invention.

The present invention provides azulenic retinoid compounds, therapeutic compositions containing such compounds, and methods for their production and use as anti-neoplasm and anti-dermatopathic agents for preventing and treating cancers and various dermatological disorders.

In accordance with one aspect of the subject invention, there is provided at least one azulenic retinoid having the general structure of a compound in accordance with the formula:

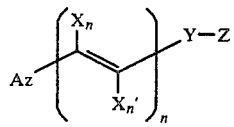
(I)

Wherein
n is an integer from 1 to 4;
each $X_n$ or $X_n'$ group can independently be taken to be H, alkyl, F, Cl or $CF_3$;
Az is an azulenic substituent group of the following general formula:

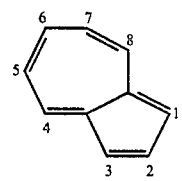

wherein
the azulenic group can be attached via any of carbons 1 to 8 to the unsaturated retinoid backbone, and
the azulene group can be further modified by additional alkyl substituents at any one or more of the remaining carbons;
the Y group can be $C_{1-10}$ straight or branched chain alkyl or an aromatic functional group of the following formula:

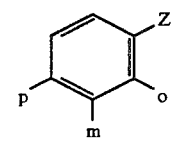

wherein the Y group can be bonded unsaturated retinoid backbone at either the para- (p), meta- (m), or ortho- (o)-position of the benzene ring, or can be des-Y; and
the Z group can be any polar end group such as aldehyde (CHO), alcohol ($CH_2OH$), acetate ($CH_2O$-$COCH_3$), or carboxylic acid ($CO_2H$) and its derivatives such as esters ($CO_2R$) and amides (CONRR');
with the provisos that:
when the Az group is azulene attached to the unsaturated retinoid backbone via the 1' carbon or guaiazulene attached to the unsaturated retinoid backbone via the 3' carbon, and n=1 or 2, then at least one of the following limitations apply:
at least one $X_n$ or $X_n'$ group is not H;
Y is not des-Y; or
z is not CHO;
when the Az group is azulene attached to the unsaturated retinoid backbone via the 2' carbon, then at least one of the following limitations apply:
when n=1, then either $X_1$ is not $CH_3$ or Y is not des-Y, or Z is not CHO; or
when n=3, then either $X_3$ is not $CH_3$ or Y is not des-Y, or Z is not CHO or $COOCH_3CH_2OH$.

Typically, representative azulenic retinoid compounds employed in the practice of the invention comprise a central $C_{2-8}$ isoprene moiety to form a retinoid backbone, an azulenic or guaiazulenic group 1'-substituted to the n'- end of the retinoid backbone and at least one methyl group independently substituted at the at the X or X' positions on the backbone. Such compounds are generally in accordance with the formula:

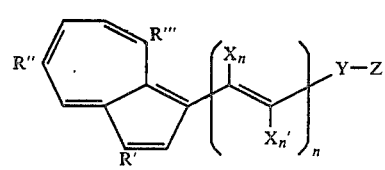
(II)

wherein each R group can independently be taken to be H or C$_{1-3}$ alkyl; and

X$_n$, X$_n'$, Y and Z are as previously defined.

More particularly, azulenic retinoid compounds of the present invention will have a C$_6$ retinoid backbone. These azulenic retinoid compounds are generally in accordance with the formula:

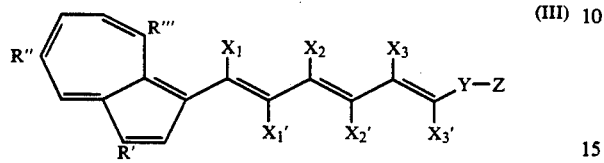
(III)

wherein
each X$_n$ or X$_n'$ group can independently be taken to be H, C$_{1-3}$ alkyl, F, Cl or CF$_3$;
Y is des-Y; and
R and Z are as previously defined.

The presently preferred azulenic retinoid compounds utilized in the practice of the present invention include those compounds of formula III as disclosed above. Conveniently, the preferred azulenic retinoid compounds, having the general structure of compounds in accordance with formula III can be subdivided into two classes.

In the first sub-class, the preferred azulenic retinoids are generally in accordance with the formula:

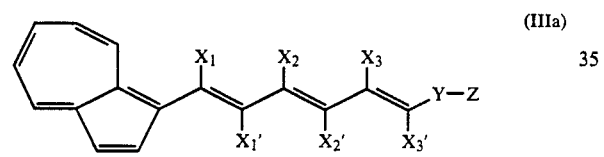
(IIIa)

Such azulenic retinoid compounds will generally comprise a central retinoid backbone of six carbons and an azulenic substituent group.

The second sub-class of presently preferred azulenic retinoid compounds are generally in accordance with the formula:

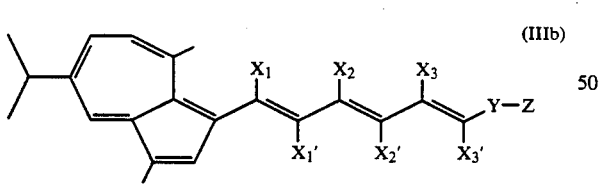
(IIIb)

These azulenic retinoid compounds differ from the azulenic retinoids in the first sub-class in that they possess a guaiazulenic substituent group.

Representative azulenic retinoid compounds of the invention include:

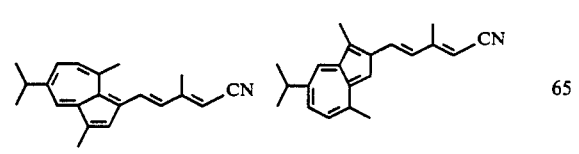

-continued

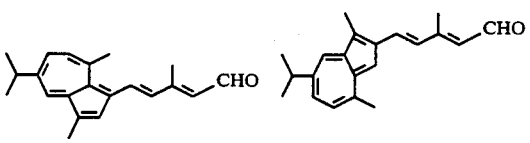
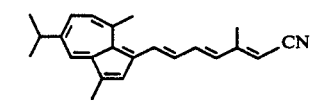
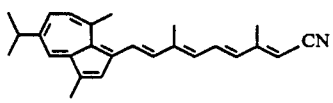
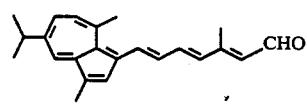
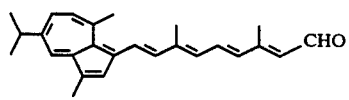
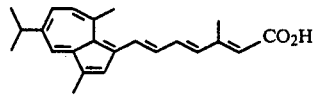
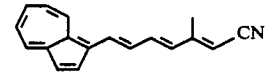
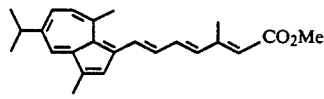
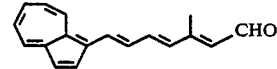
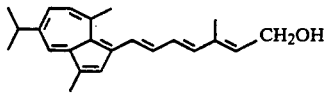
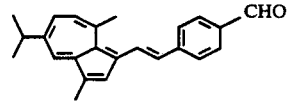
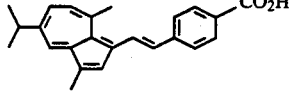
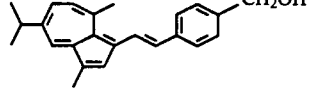
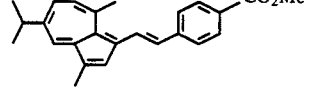

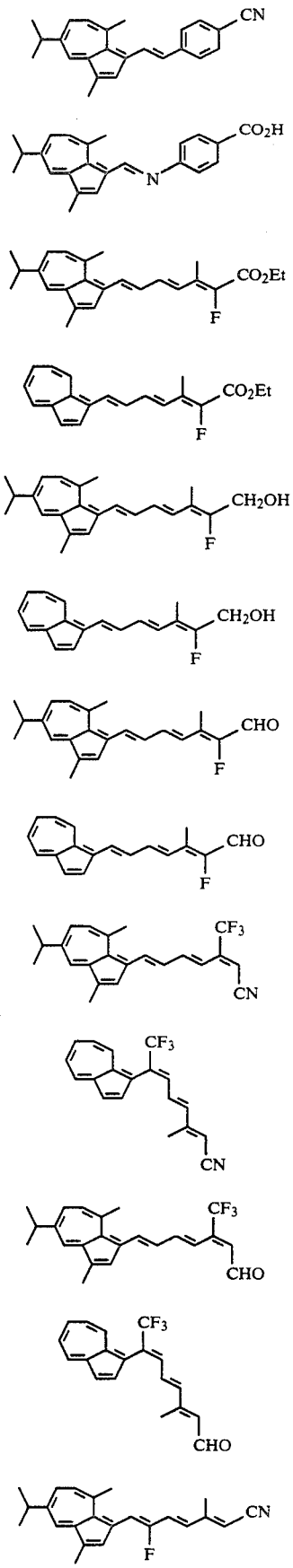
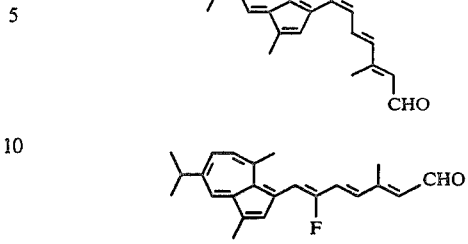

Azulenic retinoid compounds within the scope of the invention can be produced in accordance with general principles of chemical synthesis well known in the art. For example, procedures for olefination of known acylated azulenes are disclosed in Liu, R. S. H. and A. E. Asato, *Methods Enzymol.* 88:506 (1982), Liu, R. S. H. and A. E. Asato, *Tetrahedron* 40:1931 (1984), and Liu, R. S. H. and A. E. Asato in "Chemistry and Biology of Synthetic Retinoids," Chapter 3, Dawson, M. I. and W. H. Okamura Eds., CRC Press, Boca Raton, Fla. (1990).

In general, the desired 1-substituted azulenic retinoid compounds of the present invention can be prepared from azulene-1-carboxaldehyde or guaiazulene-1-carboxaldehyde which are obtained in high yield from azulene or guaiazulene by treatment with triethyl orthoformate in the presence of a catalytic amount of boron trifluoride etherate in petroleum ether (as described by Triebs, W., *Tetrahedron Lett.* 47:4707 (1967)).

The acetylated compounds, 1-acetylazulene and 1-acetylguaiazulene, are obtained from azulene and guaiazulene by their reaction with acetic anhydride (stannic chloride catalyst) or acetyl chloride (boron trifluoride etherate catalyst) in good yields (according to the procedures outlined in Anderson, Jr., A. G., et al., *J. Am. Chem. Soc.* 75:4980 (1953). The fluorinated azulenes, 1-trifluoroacetylazulene and 1-trifluoroacetylguaiazulene, are prepared in high yield by their reaction with trifluoroacetic anhydride in methylene chloride (as described by Anderson, Jr., A. G. and R. G. Anderson, *J. Org. Chem.* 27:3578 (1962)).

The elaboration of the retinoid side chain is carried out by employing conventional synthetic methodologies. Thus, a typical synthetic protocol involves the condensation of the 1-acylazulene with the lithium salt of diethyl cyanomethylphosphonate (a $C_2$-chain extension reagent) gives the 3-(1-azulenyl or 1-guaiazulenyl)-2-propenenitrile, which is converted to its corresponding aldehyde derivative by treatment with diisobutylaluminum hydride (DIBAL) in ether, tetrahydrofuran (THF), or other suitable solvents, in acceptable yields. Thereafter, condensation of this aldehyde (after conventional column chromatographic separation and purification) with the lithium salt of diethyl 3-cyano-2-methyl-2-propenylphosphonate (a $C_5$-olefination reagent) in THF affords the corresponding 7-(1-azulenyl or 1-guaiazulenyl)-3-methyl-2,4,6-heptatrienenitrile. After purification, reduction of this nitrile with DIBAL affords 7-(1-azulenyl or 1-guaiazulenyl)-3-methyl-2,4,6-heptatrienal as a mixture of 2E- and 2Z-isomers. Final purification by high performance liquid chromatography (HPLC) using 20% ethyl acetate in hexanes on a silica gel column separates the mixture into its isomerically pure forms.

For numerous azulenic retinoid compounds of the present invention, preparation in accordance with the disclosed protocols will generally provide mixtures of isomers, which can generally be resolved, or partially purified, from the mixture by preparative HPLC, generally as described in Liu, R. S. H. et al., *J. Am. Chem. Soc.* 99:8095 (1977), and characterized by $^1$H-, $^{19}$F-, and $^{13}$C-nuclear magnetic resonance (NMR), as well as ultraviolet-visible (uv-vis) and infrared (IR) absorption spectroscopy. The use of HPLC as an analytical tool for the separation and purification of complex mixtures of retinoids is well documented. For example, the differences between straight (normal) and reversed phase conditions for the quantitative fractionation of mixtures of retinol (Vitamin A) isomers have been described (Stancher, B. and F. Zonta, *J. Chromatography*, 234:244 (1982)). The analytical isocratic normal phase separation of retinal photomixtures has also been described Liu, R. S. H. and A. E. Asato, *Methods Enzymol.* 88:506 (1982); Bruening, R. C. et al., *J. Chromatography* 361:437 (1986); and others). A comprehensive survey of HPLC separations, both normal and reversed phase, of retinoids in general has been reported by C. A. Frolik and J. A. Olson in The Retinoids, Sporn, M. B. et al. Eds., Academic Press, NY, Vol. 1, Chap. 4, pp. 198–211 (1984).

Figure 2A:
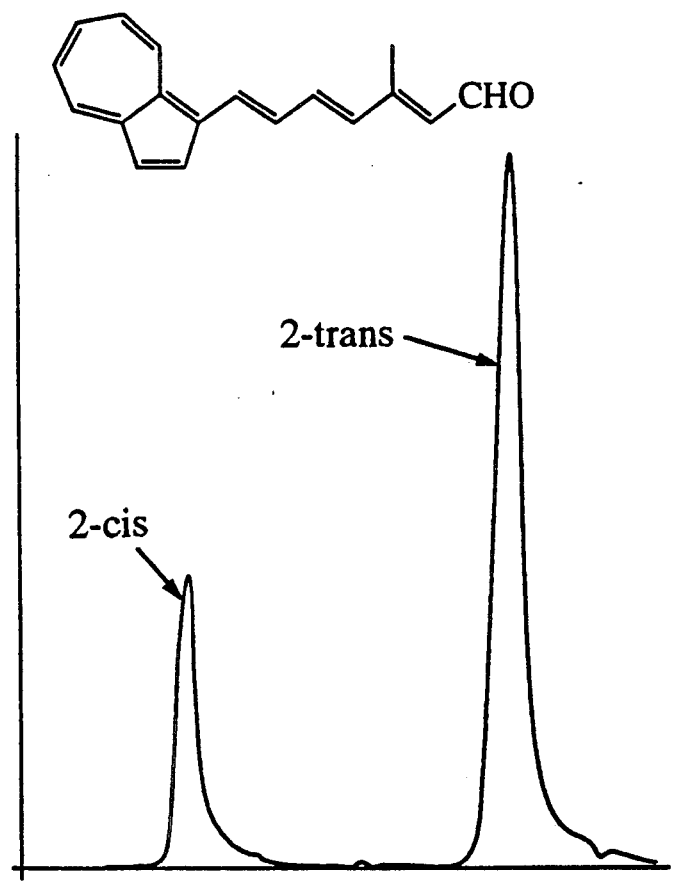
FIGS. 2A and B are diagrammatic representations of HPLC separation profiles of isomers of selected azulenic retinoid compounds of the invention.
Figure 2B:
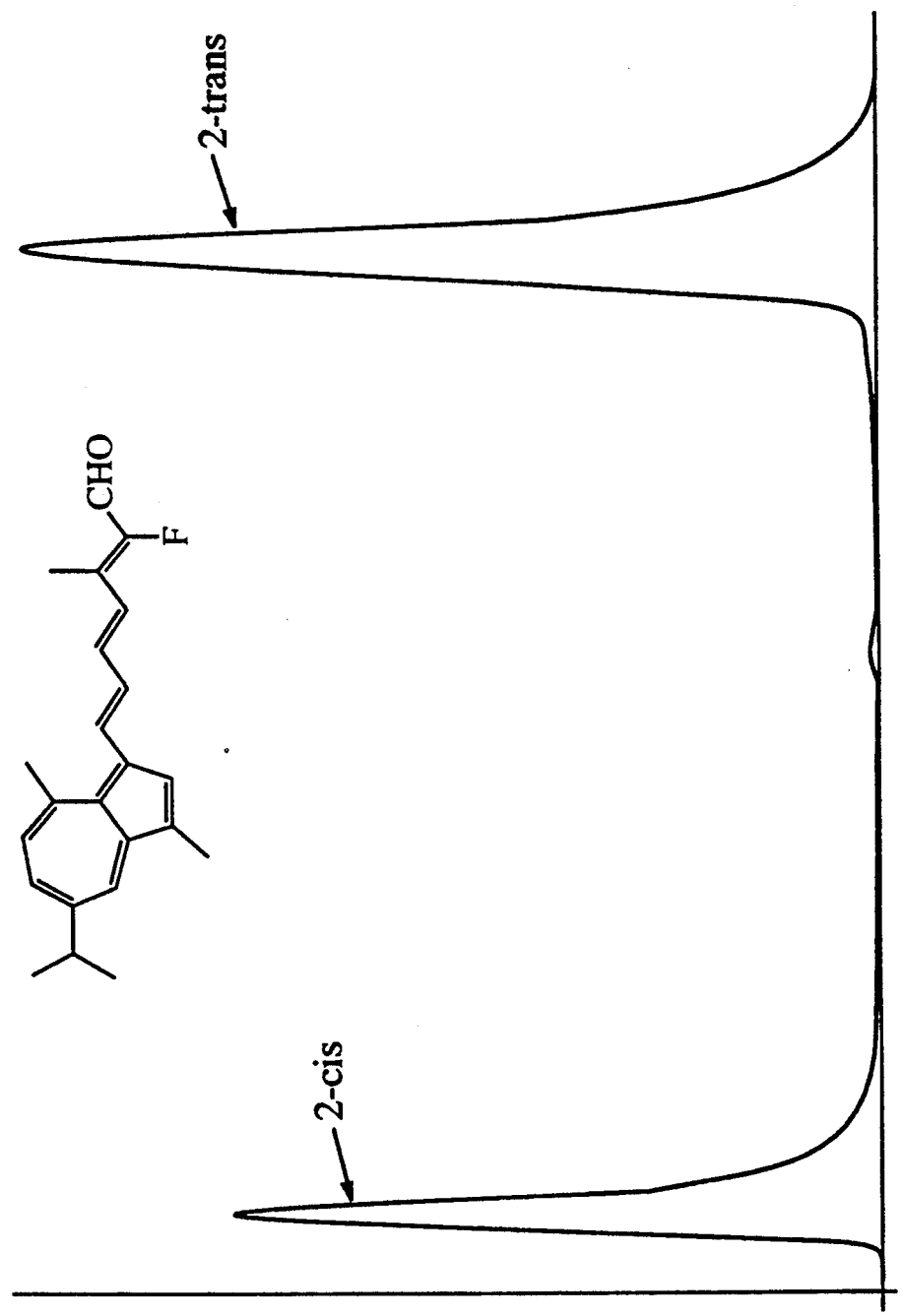

Azulenic retinal analogs can be analytically and preparatively separated for example by normal phase HPLC, typically using a silica gel column such as the 5μ 10×250 mm Microsorb ® column available from Rainin Instrument Company. The azulenic retinals, being somewhat more polar than native retinal, typically require binary solvent mixtures of increased polarity such as 20–30% ethyl acetate/hexanes. As can be seen in FIGS. 2A and 2B, the stereoisomers of azulenic retinoid compounds of the invention can be resolved or partially purified in the manner herein described.

It will also be readily understood that other means known in the art will be found useful to separate desired isomers from such mixtures, such as chiral column affinity purification as described in Wainer, I. W. and T. O. Doyle, "Stereoisomeric Separations," Liquid Chromatography 2 (February 1984) or in Regis Lab Notes, Regis Chemical Co., Morton Grove, Ill., pp. 6–7 (January 1984). Alternatively, the desired stereoisomer can be synthesized directly by stereo-specific synthesis or produced by chemical or photochemical isomerization in accordance with principles generally known in the art.

Also provided in accordance with aspects of the invention are pharmaceutical compositions useful as anti-cancer and cancer-prevention agents, anti-dermatopathic agents and/or immunomodulators, which compositions contain the above-recited azulenic retinoid compounds together with a pharmaceutically acceptable carrier. Administration of therapeutically effective doses of these compositions can provide effective delivery of the above-recited biological activities to mammalian hosts.

These azulenic retinoid compositions are found to be effective in preventing and reversing neoplasms and various dermatological disorders. The azulenic retinoid compositions are generally employed either prophylactically or therapeutically.

Compounds and compositions of the present invention which are shown to have the above recited physiological effects can find use as therapeutic agents in the treatment of various disorders such as, for example, cancer, acne, psoriasis, and other dermatological conditions pertaining to the repair and effacement of wrinkles, inflammation, allergies, and other applications in medicinal and non-medicinal areas including hair treatments, suppositories, cosmetics, and as optical recording media.

Thus, a further aspect of the present invention provides compositions containing a therapeutically effective amount of at least one azulenic retinoid compound of the present invention, including the nontoxic addition salts thereof, which may, alone, serve to provide the above-recited therapeutic benefits. Such compositions can also be provided together with physiologically tolerable liquid, gel or solid carriers, diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 μg/kg, more usually 0.01 to 100 μg/kg, of the host body weight. Alternatively, dosages within these ranges can be administered by constant infusion over an extended period of time, usually exceeding 24 hours, until the desired therapeutic benefits have been obtained.

The azulenic retinoid compounds may be formulated into the therapeutic compositions as neutral or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups (for example in a protonated azulenic retinoid Schiff base) and will generally be formed with inorganic acids such as, for example, hydrochloric or phosphoric acids, or organic acids such as acetic, oxalic, tartaric, mandelic, and the like.

Such compositions are typically prepared as oral formulations, either as liquid solutions or suspensions, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiological tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

The compositions are conventionally administered orally, for example in an acceptable carrier and, optionally, including flavorings. Alternatively, the compositions are administered parenterally, by injection, for example, either subcutaneously or intravenously. Additional formulations which are suitable for other modes of administration, such as topical administration, include salves, tinctures, creams, lotions, sprays, suppositories, and, in some cases, intranasal aerosols. For salves and creams, traditional binders, carriers and excipients may include, for example, polyalkylene glycols or triglycerides; such salves and creams may be formed from mixtures containing the active ingredient in the range of 0.05% to 5.0%, preferably about 0.1% to 2%.

The following examples serve to illustrate certain preferred embodiments and aspects of the present invention and are not to be construed as limiting the scope thereof.

Experimental

In the experimental disclosure which follows, all weights are given in grams (g), milligrams (mg), micrograms (μg) or moles (mol), all concentrations are given as percent by volume (%), molar (M), millimolar (mM) or micromolar (μM), and all volumes are given in liters (L) or milliliters (mL), unless otherwise indicated.

The following examples demonstrate the preparation of precursors to synthesis of azulenic retinoid compounds, the synthesis of azulenic retinoid compounds, the preparation of compositions containing such compounds and their use as therapeutic agents in accordance with the invention.

The compounds azulene-1-carboxaldehyde and guaiazulene-1-carboxaldehyde are useful as precursors to the synthesis of azulenic retinoid compounds of the present invention. These compounds are obtained in high yield from azulene or guaiazulene by treatment with an excess (e.g. a five-fold molar excess) of triethyl orthoformate or trimethyl orthoformate in the presence of a catalytic amount of boron trifluoride etherate in petroleum ether in accordance with the protocol described by Triebs, W., *Tetrahedron Lett.* 47:4707 (1967).

The acetylated compounds 1-acetylazulene and 1-acetylguaiazulene are also useful as precursors to the synthesis of azulenic retinoid compounds of the present invention. These compounds are obtained in good yields from azulene and guaiazulene respectively by their reaction with a very large excess (e.g. a 23-fold molar excess) of acetic anhydride (employing stannic chloride as catalyst) or a large excess (e.g. a 10-fold molar excess) of acetyl chloride (employing boron trifluoride etherate as catalyst) in accordance with the techniques outlined in Anderson, Jr., A. G., J. A. Nelson and J. J. Tazuma, *J. Am. Chem. Soc.* 75:4980 (1953).

The fluorinated azulenes, 1-trifluoroacetylazulene and 1-trifluoroacetylguaiazulene are also useful as precursors to the synthesis of azulenic retinoid compounds of the present invention. These compounds are obtained in high yield by the reaction of azulene or guaiazulene with an excess (e.g. a 1.5 to 3-fold molar excess) of trifluoroacetic anhydride in methylene chloride in accordance with the techniques outlined in Anderson, Jr., A. G. and R. G. Anderson, *J. Org. Chem.* 27:3578 (1962).

The following examples demonstrate the synthesis of azulenic retinoid compounds in accordance with the present invention. In these examples, reference will be made to various compounds depicted in the Figures by resort to the corresponding reference numerals.

EXAMPLE 1

Figure 3:
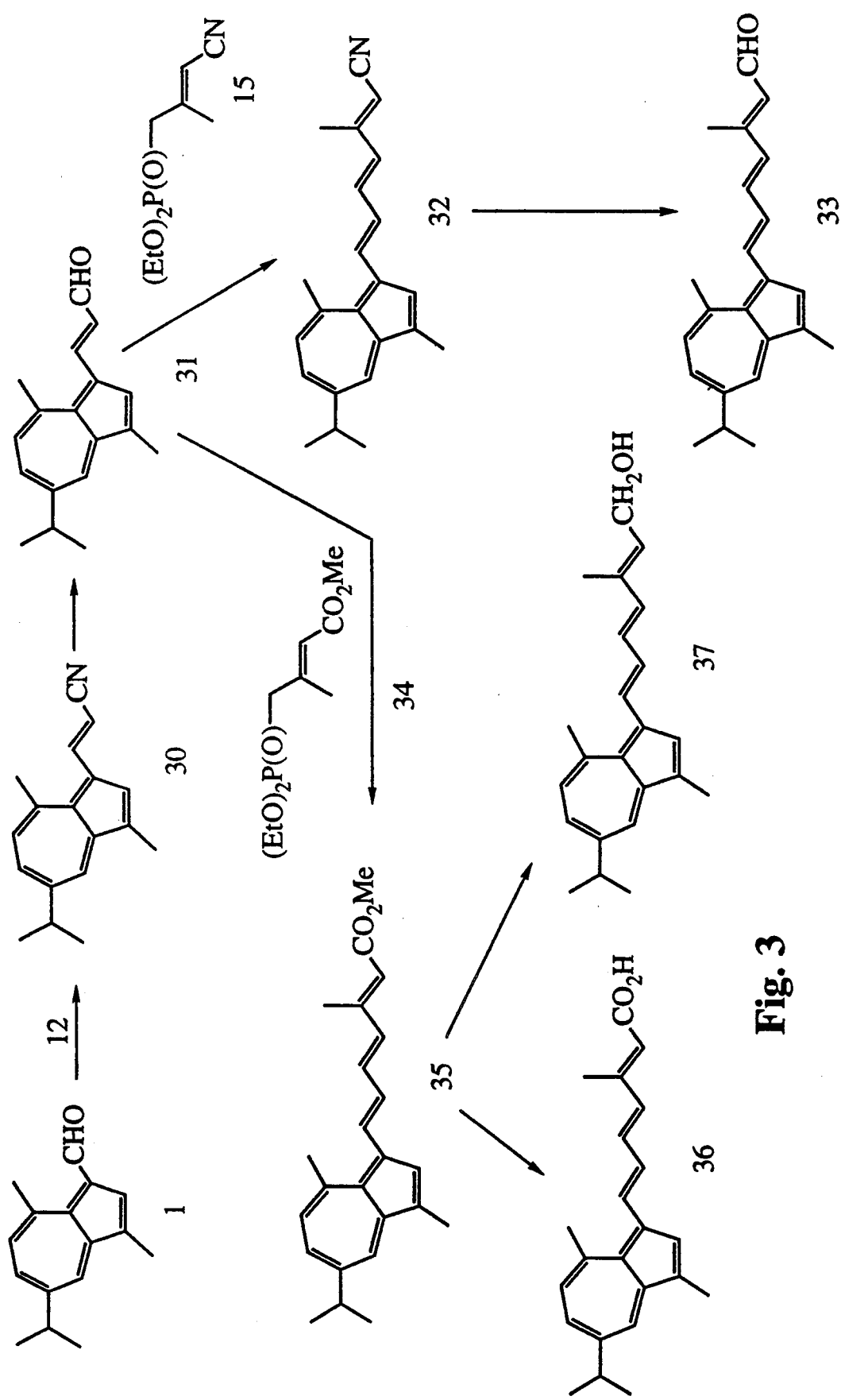

The azulenic retinoid compound of the invention identified by the formula:

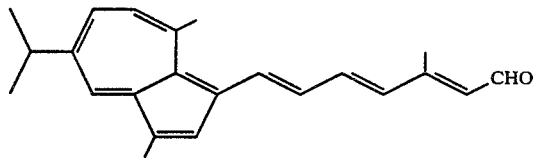

is prepared from guaiazuline-1-carboxaldehyde in accordance with the present disclosure, with particular reference to FIG. 3.

Guaiazulene-1I-carboxaldehyde 1 is prepared according to the procedure of W. Treibs, supra, (1967), as follows: To a stirred solution of guaiazulene (4.5 g, Aldrich Chemical Company) and trimethyl orthoformate (10 mL) in dichloromethane (40 mL) at RT is added boron trifluoride etherate (6 mL) over 2 minutes. The initial blue color reverts to yellow brown, whereupon the reaction mixture solidifies. After 30 min. dichloromethane (40 mL) is added to redissolve the solid mass and the resultant dark green solution is stirred for an additional 60 min. At this time, the solution is cooled to 0° C., water (100 mL) is added over 2 min. followed by dilute ammonium hydroxide (10mL, 6M). After brief swirling, the purple organic layer is separated and the aqueous layer extracted with three 25 mL portions of ether-hexanes (1:1). The combined organic layers are successively backwashed with two 25 mL portions of water followed by brine solution (25 mL). After drying in magnesium sulfate (MgSO4), the solution is concentrated in vacuo to afford crude compound 1 (5 g) as a purple crystalline mass. Recrystallization from cyclohexane (150 mL) at 0° C. overnight gives the desired aldehyde (3.83 g) as shiny purple needles. Spectroscopic data for 1 (NMR, uv) is in complete agreement with published data for this compound.

Figure 8:
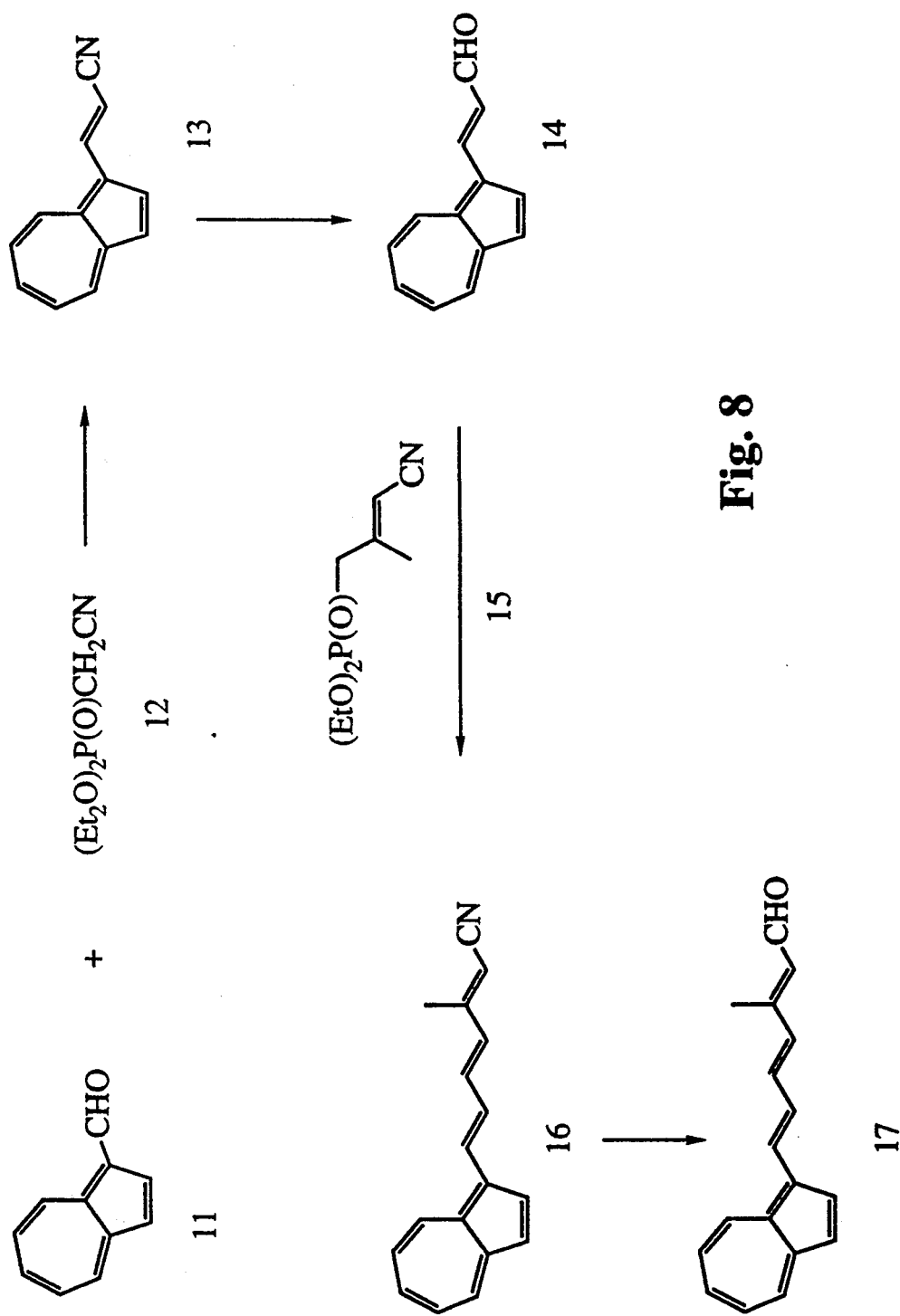

To the lithium salt of diethyl cyanomethylphosphonate (prepared from diethyl cyanomethylphosphonate 12 (2.12 g) as depicted in FIG. 8 and butyllithium (5 mL, 2.5 M in hexane)) in tetrahydrofuran (THF) (25 mL) is added guaiazulene-1-carboxaldehyde 1 (1.14 g) in THF (10 mL) at −78° C. After stirring for 1 hour at room temperature (RT), the reaction mixture is worked up by quenching with dilute citric acid, extraction with ether-hexanes (1:1), backwashing of the combined organic layers with water followed by brine solution, drying (MgSO4), filtration and concentration in vacuo to give the crude nitrile 30 as a dark green solid. Recrystallization from ethyl acetate-pentane gives pure 3-(1-guaiazulenyl)-2-propenenitrile 30 (0.70 g) as dark green needles.

The reduction of nitrile 30 (0.70 g) with excess diisobutylaluminum hydride (DIBAL, 3 mL, 1M in hexane, Aldrich Chemical Company) in ether-dichloromethane-pentane solution at −78° C. for 1 hour followed by wet silica gel work up gives the corresponding crude aldehyde 31 (0.945 g) as a dark green-black solid. Trituration with boiling hexanes and filtration affords pure 3-(1-guaiazulenyl)-2-propenal 31 (0.493 g) as a black solid.

To a stirred, cold (−78° C.) solution of LDA (prepared from diisopropylamine (1.4 mL) and butyllithium (3 mL, 2.5M in hexane, Aldrich Chemical Company) in THF (10 mL)) is added diethyl 3-cyano-2-methyl-2-propenylphosphonate 15 (1.52 g) in THF (15 mL). To the resultant brown mixture is added after 10 min. a solution of 3-(1-guaiazulenyl)-2-propenal 31 (0.945 g) in THF (20 mL). After stirring at RT for 1 hour the reaction is worked up by treatment with aqueous citric acid, ether-hexane (1:1) extraction, backwashing with water and brine, drying over magnesium sulfate and concentration in vacuo. After isolation of the crude product, filtration through a pad of silica gel using ether-dichloromethane-pentane (1:1:2) affords the desired 7-(1-guaiazulenyl)-3-methyl-2,4,6-heptatrienenitrile 32 as a 2-cis/2-trans-mixture which is immediately used in the following conversion.

Reduction of the guaiazulenic triene nitrile 32 (approximately 1 g) in dichloromethane-ether (25 mL) at −78° C. with DIBAL (10 mL, 1M in hexane) and stirring the mixture at RT for 1 hour gives the corresponding crude aldehyde after work up with wet silica gel. Column chromatography on silica gel using 20% ether-pentane with added dichloromethane gives the desired product as a black solid, 7-(1-guaiazulenyl)-3-methyl-2,4,6-heptatrienal 33.

EXAMPLE 2

The azulenic retinoid compound of the invention identified by the formula:

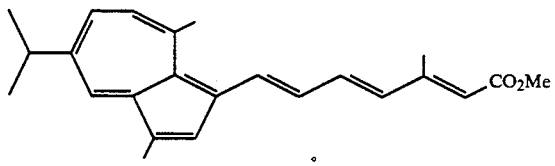

is prepared from guaiazulene-1-carboxaldehyde generally in accordance with the method outlined in FIG. 3, as follows: To the lithium salt of diethyl cyanomethylphosphonate (prepared from diethyl cyanomethylphosphonate 12 (2.12 g) and butyllithium (5 mL, 2.5M in hexane)) in THF (25 mL) is added guaiazulene-1-carboxaldehyde 1 (1.14 g) in THF (10 mL) at −78° C. After stirring for 1 hour at RT, the reaction mixture is worked up by quenching with dilute citric acid, extraction with ether-hexanes (1:1), backwashing of the combined organic layers with water followed by brine solution, drying (MgSO4), filtration and concentration in vacuo to give the crude nitrile 30 as a dark green solid. Recrystallization from ethyl acetate-pentane gives pure 3-(1-guaiazulenyl)-2-propenenitrile 30 (0.70 g) as dark green needles.

The reduction of nitrile 30 (0.70 g) with excess DIBAL (3 mL, 1M in hexane) in ether-dichloromethane-pentane solution at −78° C. for 1 hour followed by wet silica gel work up gives the corresponding crude aldehyde 31 (0.945 g) as a dark green-black solid. Trituration with boiling hexanes and filtration affords pure (3-1-guaiazulenyl)-2-propenal 31 (0.493g) as a black solid.

To a stirred, cold (−78° C.) solution of LDA (prepared from diisopropylamine (2.4 mL) and butyllithium (6 ml, 2.5M in hexane) in THF (20 mL) is added a solution of methyl 4-diethoxyphosphinyl-3-methyl-2-butenoate 34 (2.75 g) in THF (20 mL). After stirring for 30 min. a solution of 3-(1-guaiazulenyl)-2-propenal 31 (1.97 g) in THF (10 mL) is added and the reaction mixture stirred an additional 30 min. at this temperature and then at RT for 2 hours. After working up by quenching with dilute citric acid and extraction with ether-dichloromethane-pentane (2:1:10), the dark crude product is column chromatographed on silica gel using 15% ether-10% dichloromethane-75% pentane to give the desired ester, methyl 7-(i-guaiazulenyl)-3-methyl-2,4,6-heptatrienoate 35 (2.28 g) as a dark solid. Further purification by recrystallization from ethyl acetate-pentane gives pure 35 (0.852 g) as purple platelets.

EXAMPLE 3

The azulenic retinoid compound of the invention identified by the formula:

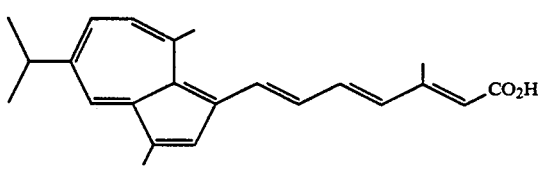

is prepared from guaiazulene-1-carboxaldehyde generally in accordance with the method outlined in Example 2, with the following modifications: Saponification of the ester 35 (0.9 g) (obtained as described in Example 2) using potassium hydroxide (5 g) in methanol (45 mL) containing some water (1 mL) and a catalytic amount of 18-crown-6 (<1 g), first at RT (20 hours) and then at gentle reflux (RT to 65° for 2.5 hours) followed by acidification with citric acid and extraction with ether-dichloromethane-pentane affords the desired guaiazulenic triene carboxylic acid 36. Recrystallization from ethly acetate-pentane gives a 2-cis/ 2-trans-isomeric mixture of 7-(1-guaiazulenyl)-3-methyl-2,4,6-heptatrienoic acid 36 (0.403g) as a brown solid.

EXAMPLE 4

The azulenic retinoid compound of the invention identified by the formula:

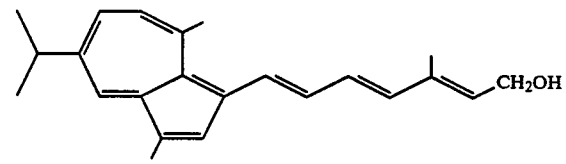

is prepared from guaiazulene-1-carboxaldehyde generally in accordance with the method outlined in Example 2, with the following modifications: To a stirred, cold (−78° C.) solution of guaiazulenic triene ester 35 (0.429 g) (obtained as described in Example 2) in 1:1 ether-pentane (50 mL) is added DIBAL (6 mL, 1M in hexane). After 30 min. the reaction is quenched with wet silica gel and, after filtration and concentration in vacuo, a dark green solid is obtained. Trituration with pentane and filtration then affords pure 7-(1-guaiazulenyl)-3-methyl-2,4,-6-heptatrien-1-ol 37 (0.334 g) as dark green platelets.

EXAMPLE 5

Figure 4:
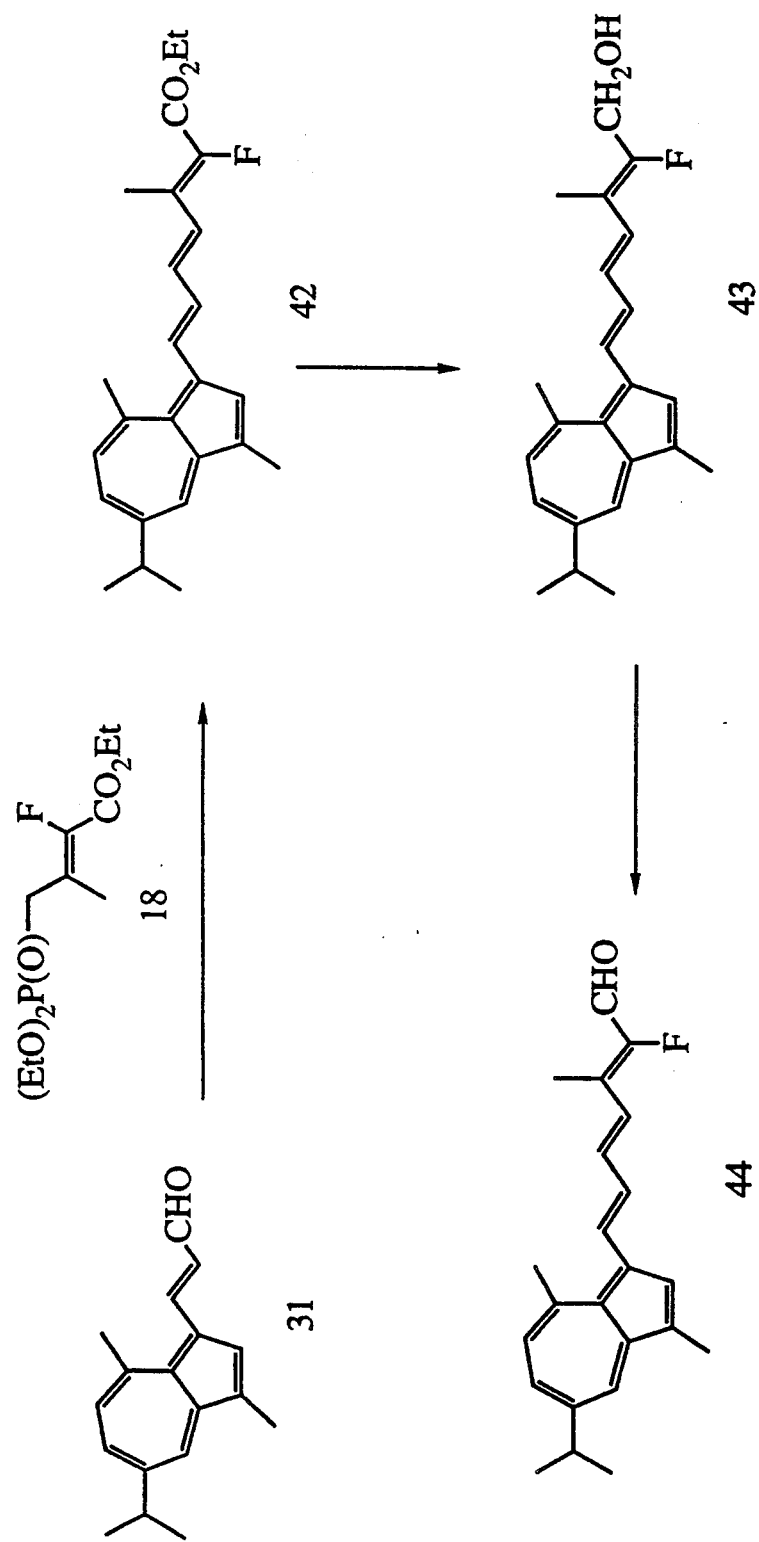

The azulenic retinoid compound of the invention identified by the formula:

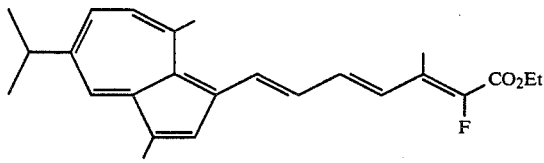

is prepared from guaiazulene-1-carboxaldehyde generally in accordance with the method outlined in FIG. 4, as follows: To a stirred, cold (−78° C.) solution of LDA (prepared from diisopropylamine (1.0 mL) and utyllithium (2.0 mL, 2.5 M in hexane) in THF (5 mL) is added a solution of ethyl 4-diethylphosphinyl-2-fluoro-3-methyl-2-butenoate 18 (1.5 g) in THF (10 mL). After 15 min. a solution of 3-(1-guaiazulenyl)-2-propenal 31 (1.22 g) in THF (15 mL) is added and the reaction mixture is stirred at RT for 2.5 hours. After conventional workup as described in Example 1 (quenching with dilute citric acid and ether-hexane extraction), there is obtained crude ethyl 2-fluoro-7-(1-guaiazulenyl)-3-methyl-2,4,6-heptatrienoate 42 (2.58 g).

EXAMPLE 6

The azulenic retinoid compound of the invention identified by the formula:

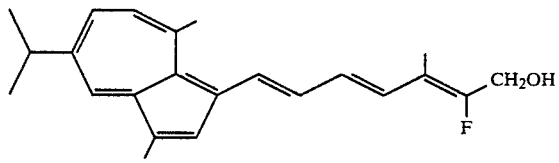

is prepared from guaiazulene-1-carboxaldehyde generally in accordance with the method outlined in FIG. 4, as follows: Ethyl 2-fluoro-7-(1-guaiazulenyl)-3-methyl-2,4,6-heptatrienoate 42 (2.58 g) which is obtained as described in Example 5 is used in the following conversion.

Reduction of guiazulenic triene fluoro ester 42 with DIBAL followed by standard wet silica gel workup gives the desired crude alcohol, 2-fluoro-7-(1-guaiazulenyl)-3-methyl-2,4,6-heptatrien-1-ol 43.

EXAMPLE 7

The azulenic retinoid compound of the invention identified by the formula:

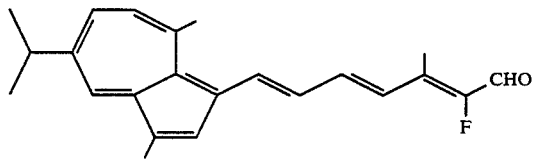

is prepared from guaiazulene-1-carboxaldehyde generally in accordance with the method outlined in FIG. 4, as follows: The crude alcohol, 2-fluoro-7-(1-guaiazulenyl)-3-methyl-2,4,6-heptatrien-1-ol 43, which is obtained as described in Example 6, is used in the following conversion without further characterization.

Treatment of the crude carbinol 43 in dichloromethane (30 mL) with activated manganese dioxide (5 g) for 5 min. at RT followed by filtration through Celite gives the desired aldehyde, 2-fluoro-7-(1-guaiazulenyl)-3-methyl-2,4,6-heptatrienal 44 as a red-black oil consisting mainly of a mixture of 2-cis- and 2-trans- isomers.

EXAMPLE 8

Figure 5:
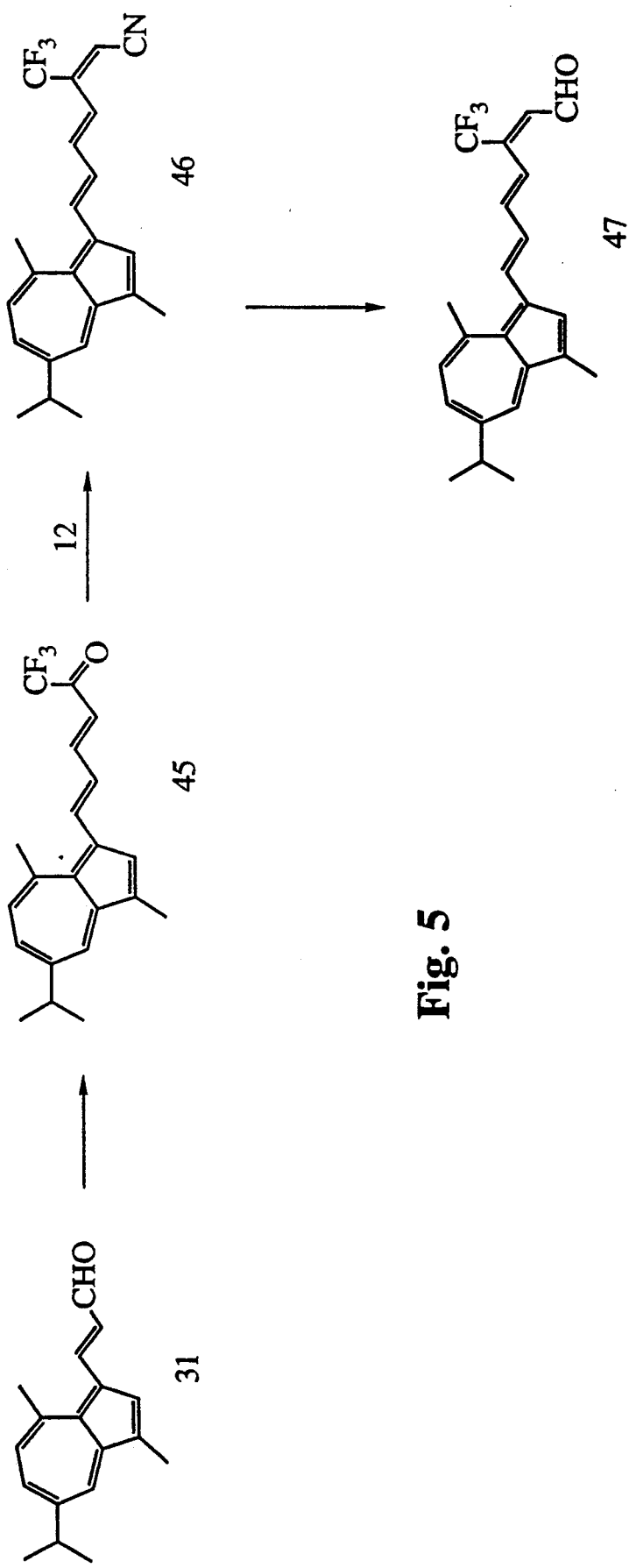

The azulenic retinoid compound of the invention identified by the formula:

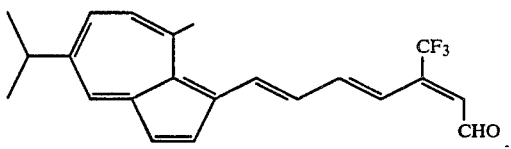

is prepared from guaiazulene-1-carboxaldehyde generally in accordance with the method outlined in FIG. 5 with the following modifications: The piperidine-acetic acid catalyzed condensation of crude 3-(1-guaiazulenyl)-2-propenal 31 (obtained as described in Example 1) with excess trifluoroacetone in THF (according to the procedure of Mead, D., R. Loh, A. E. Asato and R. S. H. Liu, Tetrahedron Letters, 26:2873 (1985)) is carried out to afford 6-(1-guaiazulenyl)-1,1,1-trifluoro-3,5-hexadien-2-one 45 as the sole product.

Chain extension of this trifluormethyl ketone using the lithuim salt of diethyl cyanomethylphosphonate 12 in THF gives the C2-chain extended fluorinated nitrile, 7-(1-guaiazulenyl)-3-trifluoromethyl-2,4,6-heptatrienenitrile 46 as a red oil consisting of the 2-cis isomer exclusively.

Reduction of the guaiazulenic trifluoromethyl nitrile 46 with DIBAL followed by wet silica gel workup gives the target 2-cis-7-(1-guaiazulenyl)-3-trifluoromethyl-2,4,6-heptatrienal 47 (approximately 125 mg crude product) as a purple oil.

EXAMPLE 9

Figure 6:
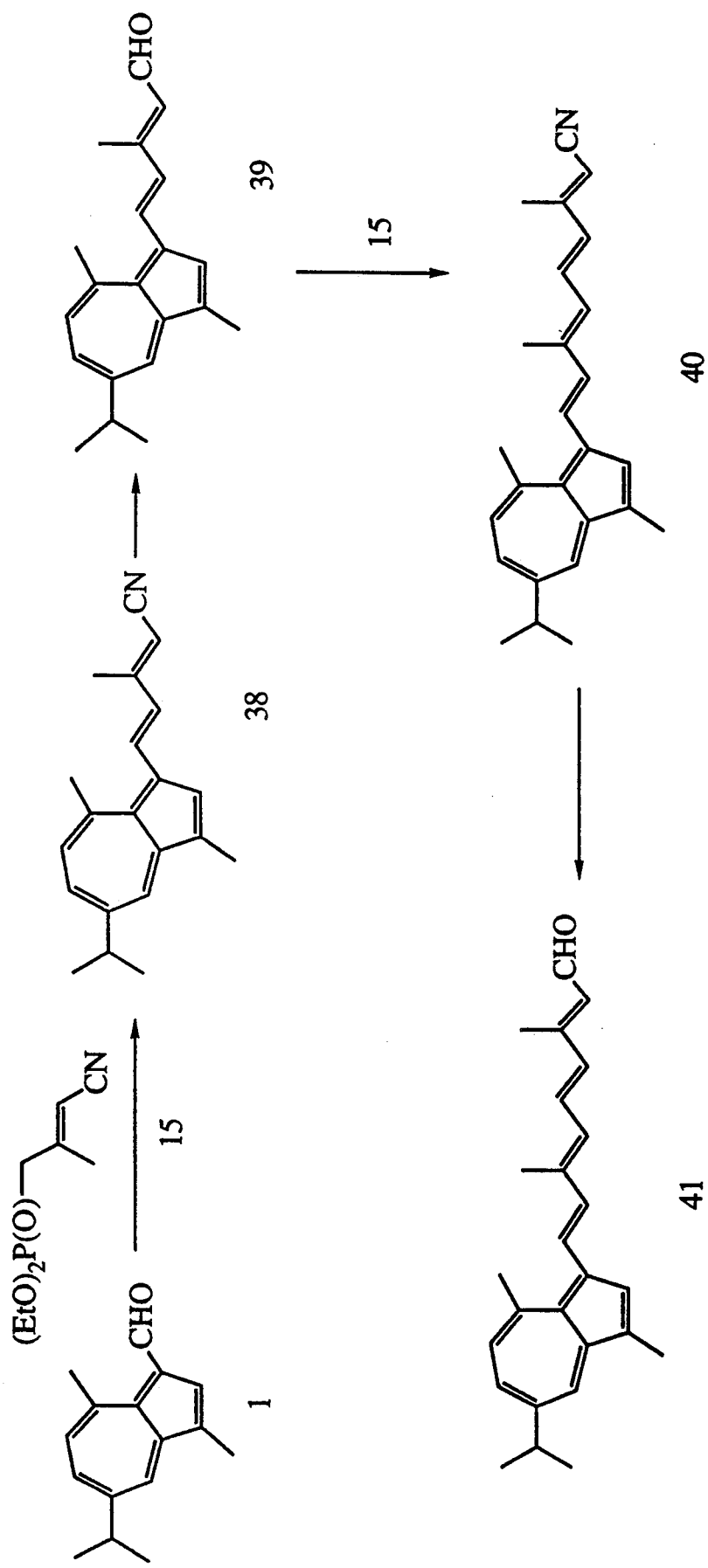

The azulenic retinoid compound of the invention identified by the formula:

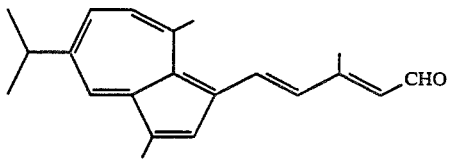

is prepared from guaiazulene-1-carboxaldehyde generally in accordance with the method outlined in FIG. 6, as follows:

To a stirred, cold (−78° C.) solution of LDA (prepared from diisopropylamine (1.8 mL) and butyllithium (4 mL, 2.5M in hexane) in THF (10 mL)) is added a solution of diethyl 3-cyano-2-methyl-2-propenylphosphonate 15 (2.17 g) in THF (10 mL). After 10 min. a solution of guaiazulene-1-carboxaldehyde 1 (1.48 g) in THF (10 mL) is added and the reaction mixture stirred at RT for 2 hours. After quenching with dilute citric acid and extraction with ether-hexanes (1:1), filtration through a pad of silica gel using 20% ether-hexanes affords 5-(1-guaiazulenyl)-3-methyl-2,4-pentadienenitrile 38 (1.05 g) in 58.3% yield as a green solid.

Reduction of nitrile 38 (1.05 g) in ether (45 mL)-dichloromethane (5 mL) at −78° C. with DIBAL (6 mL, 1M in hexane) for 45 min, quenching with wet silica gel followed by column chromatography on silica gel using 15–33% ether in hexane (with added dichloromethane to initially dissolve the crude product) gives the desired aldehyde, 5-(1-guaiazulenyl)-3-methyl-2,4-pentadienal 39 (0.566 g) as brown (brick red) needles.

EXAMPLE 10

The azulenic retinoid compound of the invention identified by the formula:

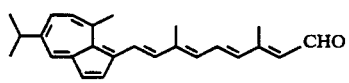

is prepared from guaiazulene-1-carboxaldehyde generally in accordance with the method outlined in FIG. 6, as follows:

To a stirred, cold (−78° C.) solution of LDA (prepared from diisopropylamine (0.42 mL) and butyllithium (0.5 mL, 2.5 M in hexane) in THF (5 mL) is added a solution of diethyl 3-cyano-2-methyl-2-propenylphosphonate 15 (0.39 g) in THF (5 mL). After 15 min. a solution of guaiazulenic dienal 39 (0.261 g) in THF (10 mL) is added and the reaction mixture stirred at RT for 2 hours. After quenching with dilute citric acid, extraction with 1:1 ether-hexane and column chromatography on silica gel using 15% ether-hexane (with some dichloromethane added to initially solubilize the crude product), the desired nitrile, 3,7-dimethyl-9-(1-guaiazulenyl)-2,4,6,8-nonatetraenenitrile 40 (0.272 g, brown powder) is obtained as an isomeric mixture.

Reduction of guaiazulenic tetraene nitrile 40 (0.139 g) in 1:1 ether-dichloromethane (50 mL), with DIBAL (2 mL, 1M in hexane) affords the desired crude aldehyde after standard wet silica gel workup. Trituration with pentane and filtration of the brown-black powder gives pure 3,7-dimethyl-9-(1-guaiazulenyl)-2,4,6,8-nonatetraenal 41 (0.133 g) as an isomeric mixture.

EXAMPLE 11

Figure 7:
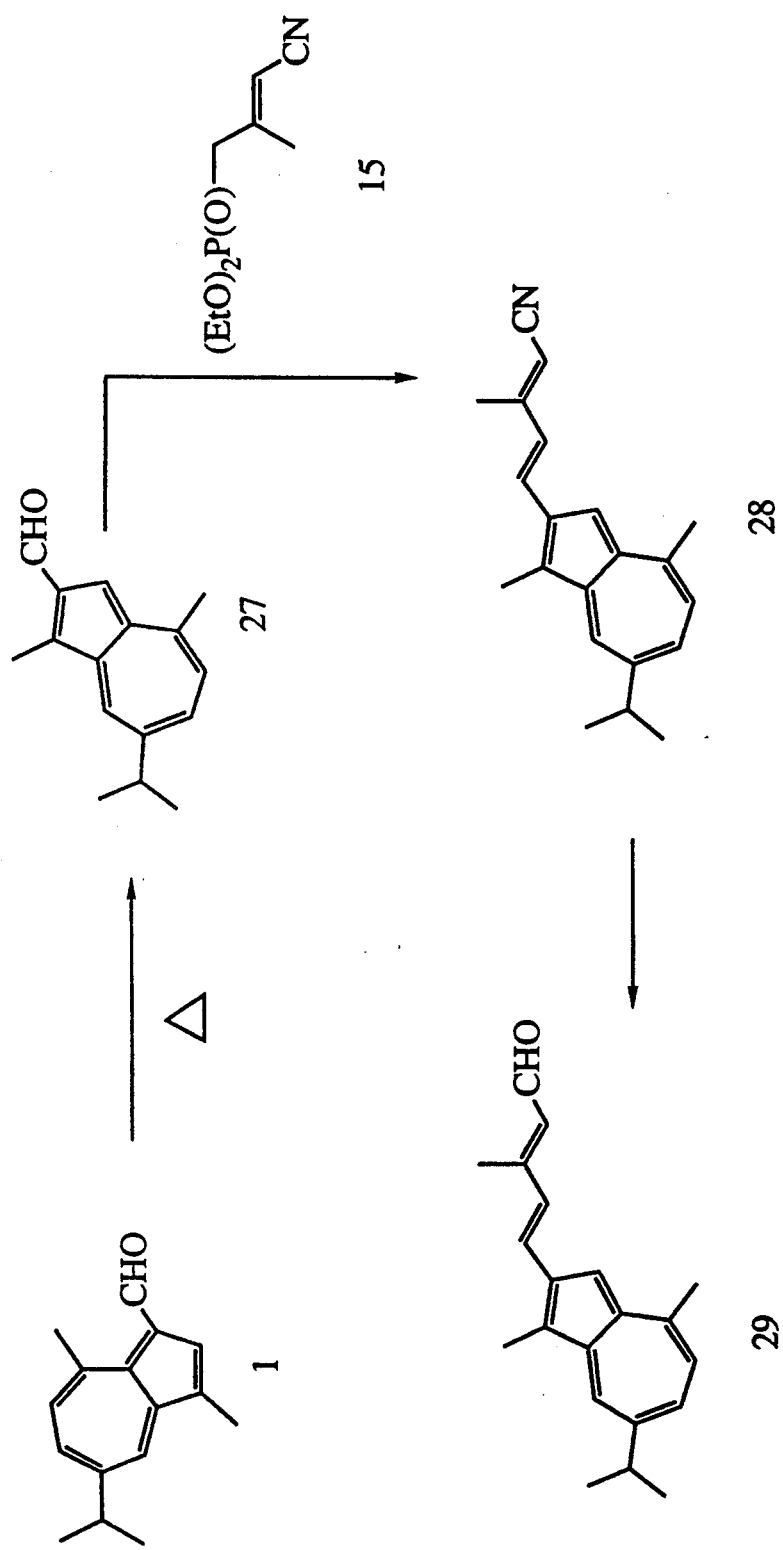

The azulenic retinoid compound of the invention identified by the formula:

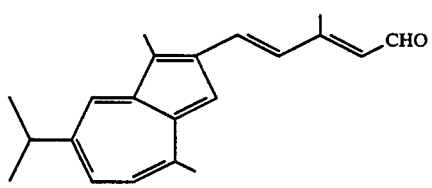

is prepared from guaiazulene-1-carboxaldehyde generally in accordance with the method outlined in FIG. 7, as follows: The thermal rearrangement of guaiazulene-1-carboxaldehyde 1 to the corresponding guaiazulene-2-carboxaldehyde isomer 27 is carried out according to the procedure of Kurokawa, S. et al., *Bull. Chem Soc. Jap.*, 48:1559 (1975). Thus, guaiazulene-1-carboxaldehyde 1 (475 mg) is heated for 90 sec in a test tube on a micro bunsen burner, air cooled for 30 sec followed by cooling in a water bath. The thermolysis mixture is digested in ether (6 mL), filtered and the ether insoluble residue washed free of colored products with additional ether (approximately 50 mL). The filtrate is concentrated in vacuo and the crude product chromatographed on silica gel using 10% ether-hexanes. An initial brilliant blue band of recovered guaiazulene is followed successively by a yellow-brown component, an emerald green component and, lastly, a brown band. The emerald green band is collected and affords the desired 2-substituted aldehyde 27 (21 mg) as a dark green oil in 4.4% isolated yield.

A repeat preparation starting from 1 (1.01 g) gives pure 27 (81.3 mg) after chromatographic purification.

To a stirred, cooled (−78° C.) solution of LDA (prepared from diisopropylamine (0.45 mL) and butyllithium (1 mL, 2.5M in hexane) in THF (10 mL)) is added a solution of diethyl 3-cyano-2-methyl-2-propenylphosphonate 15 (0.5 g) in THF (5 mL) to give the corresponding lithium salt. A solution of guaiazulene-2-carboxaldehyde 27 (81 mg) in THF (5 mL) is then added and after stirring at RT for 1 hour the reaction mixture is worked up in the conventional manner as previously described. Separation from polar impurities (e.g., excess phosphonate 15) is effected by filtration through a pad of silica gel using 20% ether-pentane. The resultant dark black nitrile 5-(2-guaiazulenyl)-3-methyl-2,4-pentadienenitrile 28 is used in the subsequent transformation without additional purification.

Thus, nitrile 28 is reduced with excess DIBAL in ether at −78° C. for 45 min. followed by wet silica gel work up. Column chromatography of the resultant dark oil on silica gel using 20% ether-hexanes gives two green bands: Band 1 consists of a mixture of 2-cis and 2-trans dienal 29 (25.8 mg) and band 2 consists of isomerically pure all-trans 5-(2-guaiazulenyl)-3-methyl-2,4-pentadienal 29 (20.3 mg) as a green oil.

EXAMPLE 12

The azulenic retinoid compound of the invention identified by the formula:

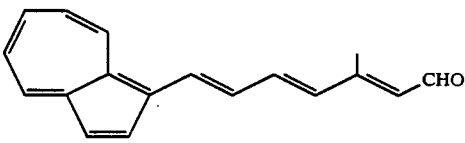

is prepared from azulene-1-carboxaldehyde generally in accordance with the method outlined in FIG. 8, as follows:

Azulene-1-carboxaldehyde 11 is prepared according to the procedure of Treibs, w. supra, (1967).

To a stirred, cooled (−78° C.) solution of lithium diethyl cyanomethylphosphonate prepared from diethyl cyanomethylphosphonate 12 (1 g) and butyllithium (2.2 mL, 2.5M solution in hexane) in THF (10 mL) is added 11 (0.31 g) in THF (10 mL). The reaction mixture is stirred at RT for 45 min. and then worked up by treatment with aqueous citric acid and extraction with ether-hexanes (1:1). The combined organic layers are backwashed with water followed by brine solution, dried (MgSO$_4$), filtered and concentrated in vacuo to give crude azulenic nitrile 13. Column chromatographic purification on silica gel using 20% ether-hexanes containing approximately 15% dichloromenthane affords pure 13 (0.32 g) as a dark blue solid in 89.9% yield.

To 3-(1-azulenyl)-2-propenenitrile 13 (0.32 g) in 1:1 dichloromethane-pentane (40 mL) cooled to −78° C. is added a solution of DIBAL (6 mL) to give a dark green solution. After stirring 45 min. at RT, the reaction mixture is quenched by the addition of a slurry of wet silica gel in ether and then concentrated in vacuo to a dark green solid. After the removal of polar impurities by filtration through a short column of silica gel using 20% ether in pentane containing 10-25% dichloromethane, the aldehyde, 3-(1-azulenyl)-2-propenal, 14 (0.3 g) is obtained.

To a stirred, cooled (−78° C.) solution of LDA (prepared from diisopropylamine (0.9 mL) and butyllithium (2 mL, 2.5M in hexane)) in THF (5 mL) is added a solution of diethyl 3-cyano-2-methyl-2-propenylphosphonate 15 (1.05 g) in THF (10 mL). To the resultant brown solution of the lithium salt of 15 is added a solution of aldehyde 14 (0.3 g, 1.65 mmol) in THF (15 mL) to afford a very dark solution which is stirred to RT over 1 hour. Normal workup (treatment with aqueous citric acid, ether-hexane (1:1) extraction, backwashing with water and brine, drying over magnesium sulfate and concentration in vacuo) gives crude 7-(1-azulenyl)-3-methyl-2,4,6-heptatrienenitrile 16. Subsequent filtration through a bed of silica gel to remove polar impurities starting with 4:1:1 pentane-ether-dichloromethane and gradually increasing the concentrations of the latter two solvents gives azulenic triene nitrile 16 (0.17 g) free of 14 and sufficiently pure for the following conversion.

The desired aldehyde, 7-(1-azulenyl)-3-methyl-2,4,6-heptatrienal 17, is obtained as a red brown solid (approximately 0.1 g) by the reduction of 16 with DIBAL in ether-dichloromethane (3:5) followed by conventional wet silica gel workup.

EXAMPLE 13

Figure 9:
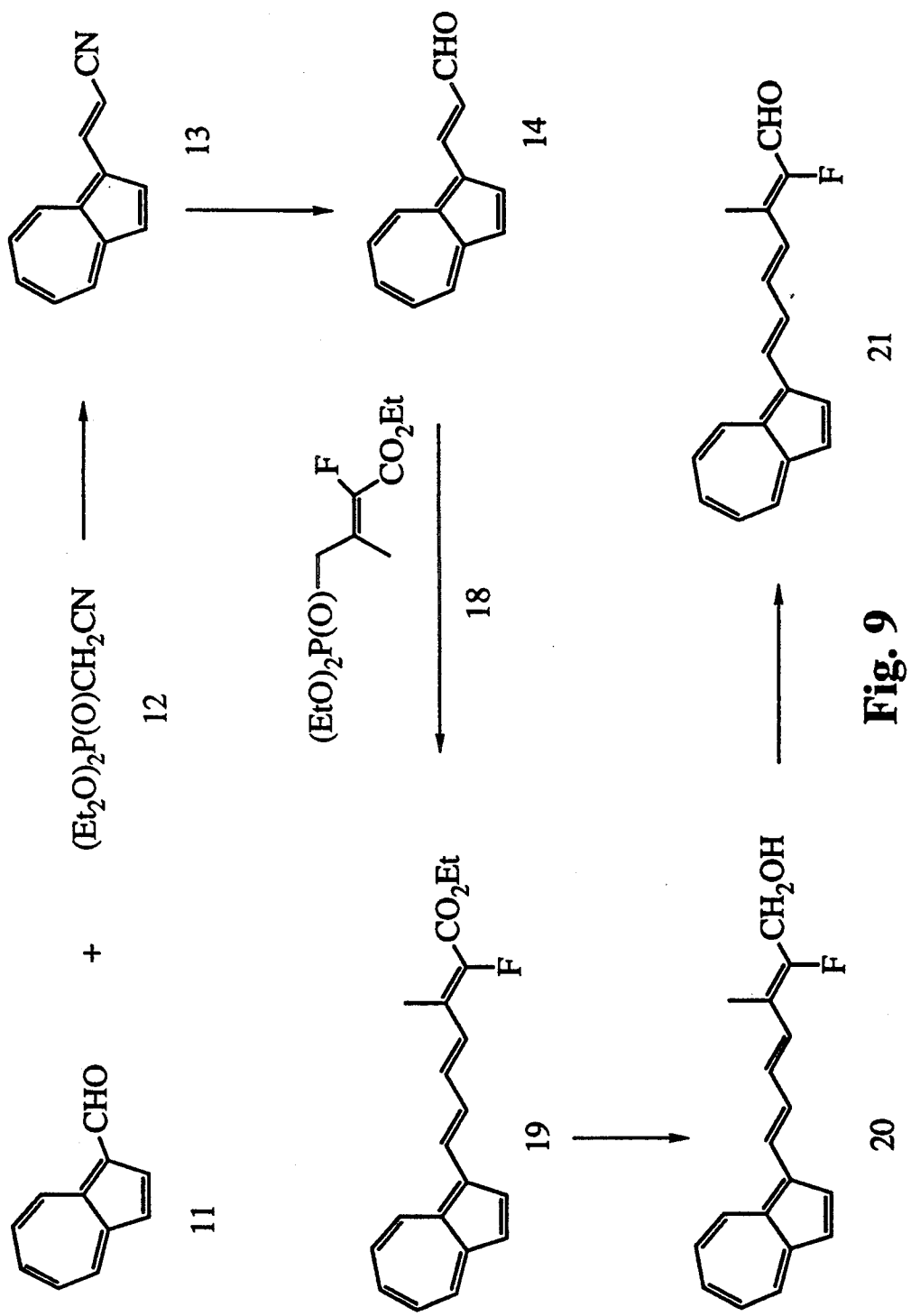

The azulenic retinoid compound of the invention identified by the formula:

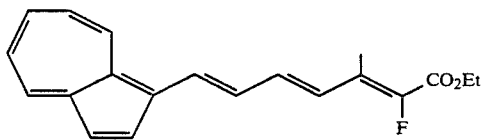

is prepared from azulene-1-carboxaldehyde generally in accordance with the method outlined in FIG. 9, as follows: From azulene-1-carboxaldehyde 11 (0.78 g) and the lithium salt of phosphonate 12 in THF is obtained the desired C2-chain-extended nitrile 13 as a blue-green solid (0.72 g after purification by silica gel column chromotography) in 80.4% yield.

Reduction of nitrile 13 with an excess of DIBAL in dichloromethane-ether-pentane (1:5:5) at −78° C. for 1 hour followed by conventional wet silica gel workup and silica gel column chromatographic purification (ether-hexanes-dichloromethane, 5:13:2) affords the desired azulenic aldehyde 14 as a green-black solid (0.615 g) in 84% yield.

To a stirred, cold (−78° C.) solution of LDA (prepared from diisopropylamine (0.8mL) and butyllithium (2.0 mL, 2.5M in hexane)) in THF (10 mL) is added a solution of ethyl 4-diethoxyphosphinyl-2-fluoro-3-methyl-2-butenoate 18 (1.5 g) in THF (8 mL) to give a clear red solution of the corresponding anion. After 10 min. a solution of aldehyde 14 (0.615 g) in THF (10 mL) is added and the reaction mixture stirred at RT for 2 hours. At this time the reaction mixture is worked up in the conventional manner to afford the desired crude azulenic fluoro ester 19 as a dark red solid. Purification by silica gel column chromatography (15% ether-hexanes plus dichloromethane to improve solubility) affords the ester, ethyl 7-(1-azulenyl)-2-fluoro-3-methyl-2,4,6-heptatrienoate 19 (0.604 g), as a dark brown solid in 58% isolated yield. NMR spectroscopy indicates that this product is a 2:1 mixture of 2-trans and 2-cis isomers.

EXAMPLE 14

The azulenic retinoid compound of the invention identified by the formula:

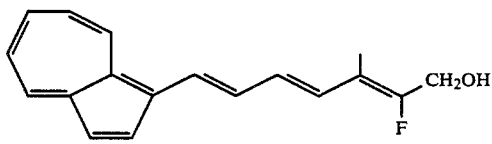

is prepared from azulene-1-carboxaldehyde generally in accordance with the method outlined in FIG. 9, as follows:

Treatment of fluoro ester 19 (0.302 g) (obtained as described in Example 13) in ether-dichloromethane (17:3) (20 mL) at −78° C. with a large excess of DIBAL (4 mL, 1M in hexane) for approximately 30 min. gives the fluoro alcohol 7-(1-azulenyl)-2-fluoro-3-methyl-2,4,6-heptatrien-1-ol 20 (0.030 g).

EXAMPLE 15

The azulenic retinoid compound of the invention identified by the formula:

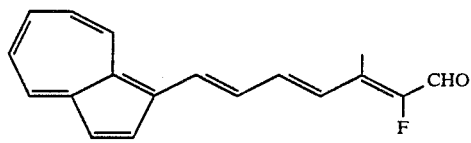

is prepared from azulene-I-carboxaldehyde generally in accordance with the method outlined in FIG. 9, as follows:

Alcohol 20 (obtained as described in Example 14) is oxidized with active manganese dioxide (5 g) in dichloromethane until the disappearance of starting material (monitored by thin layer chromatography on silica gel, dichloromethane solvent) affords the desired product, 7-(1-azulenyl)-2-fluoro-3-methyl- 2,4,6-heptatrienal, 21 , as a 2-cis/2-trans mixture as determined by NMR spectroscopy.

EXAMPLE 16

Figure 10:
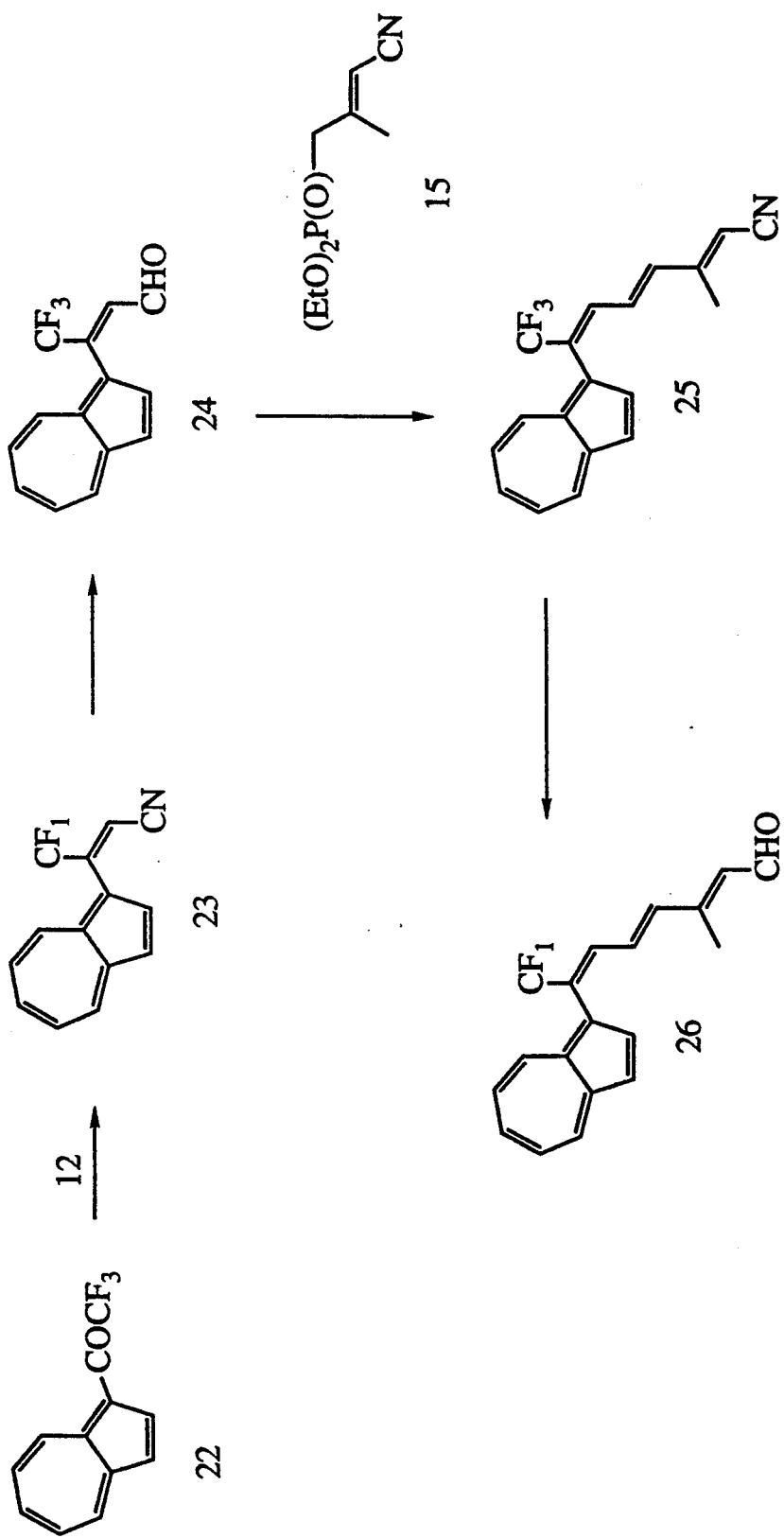

The azulenic retinoid compound of the invention identified by the formula:

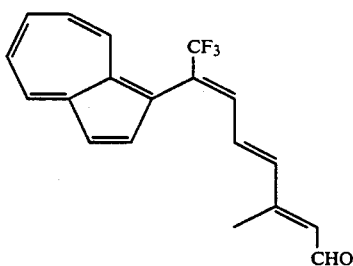

is prepared from 1-trifluoroacetylazulene in accordance with the method outlined in FIG. 10, as follows:

The preparation of I-trifluoroacetylazulene 22 is carried out according to the protocol described by Anderson, Jr., A. G. and R. G. Anderson, *J. Org. Chem.* 27:3578 (1962). Thus, brief treatment of azulene (0.82 g) with trifluoroacetic anhdride (1.5 mL) in dichloromethane (30mL) at RT gives the desired 1-azulenyl trifluoromethylketone as the sole product.

To a stirred, cold (−78° C.) solution of LDA (from diisopropylamine (2.6 mL) and butyllithium (6 mL, 2.5M in hexane) in THF (10 mL)) is added a solution of diethyl cyanomethylphosphonate 12 (2.65 g) in THF (15 mL). To the resultant solution of lithium diethyl cyanomethylphosphonate is added ketone 22 in THF (10 mL) and the mixture stirred to RT over 2 hours. After normal workup, the desired nitrile 3-(10azulenyl)-4,4,4-trifluoro-2-butenenitrile 23 is obtained as a purple solid. Fluorine NMR spectroscopy indicates the presence of a 3:2 cis-trans mixture: FMR (CDCl$_3$, CFCl$_3$ internal standard): −62.3 (singlet) and −66.7 ppm (singlet) in 2:3 ratio for the 2Z (2-trans) and 2E (2-cis) isomers, respectively.

From the reduction of nitrile 23 in ether at −78° C. with excess DIBAL followed by conventional wet silica gel workup is obtained the corresponding aldehyde, 3-(1-azulenyl)-4,4,4-trifluoro-2-butenal 24 as an isomeric (2-cis/2-trans) mixture in 3:2 ratio.

Reaction of crude 24 with the lithium salt of 15 gives the C5-chain extended product, 7-(1-azulenyl)-3-methyl-8,8,8-trifluoro-2,4,6-octatrienonitrile 25, which is immediately used in the next step of the reaction sequence.

Thus, treatment of nitrile 25 with DIBAL gives the corresponding aldehyde, 7-(1-azulenyl)-3-methyl-8,8,8-trifluoro-2,4,6-octatrienal 26 as a brown-black solid. Silica gel column chromatography liberates the desired aldehyde from impurities, but NMR spectroscopy indicates the presence of several isomers.

Final purification is carried out by normal phase HPLC, as described previously.

EXAMPLE 17

Figure 11:
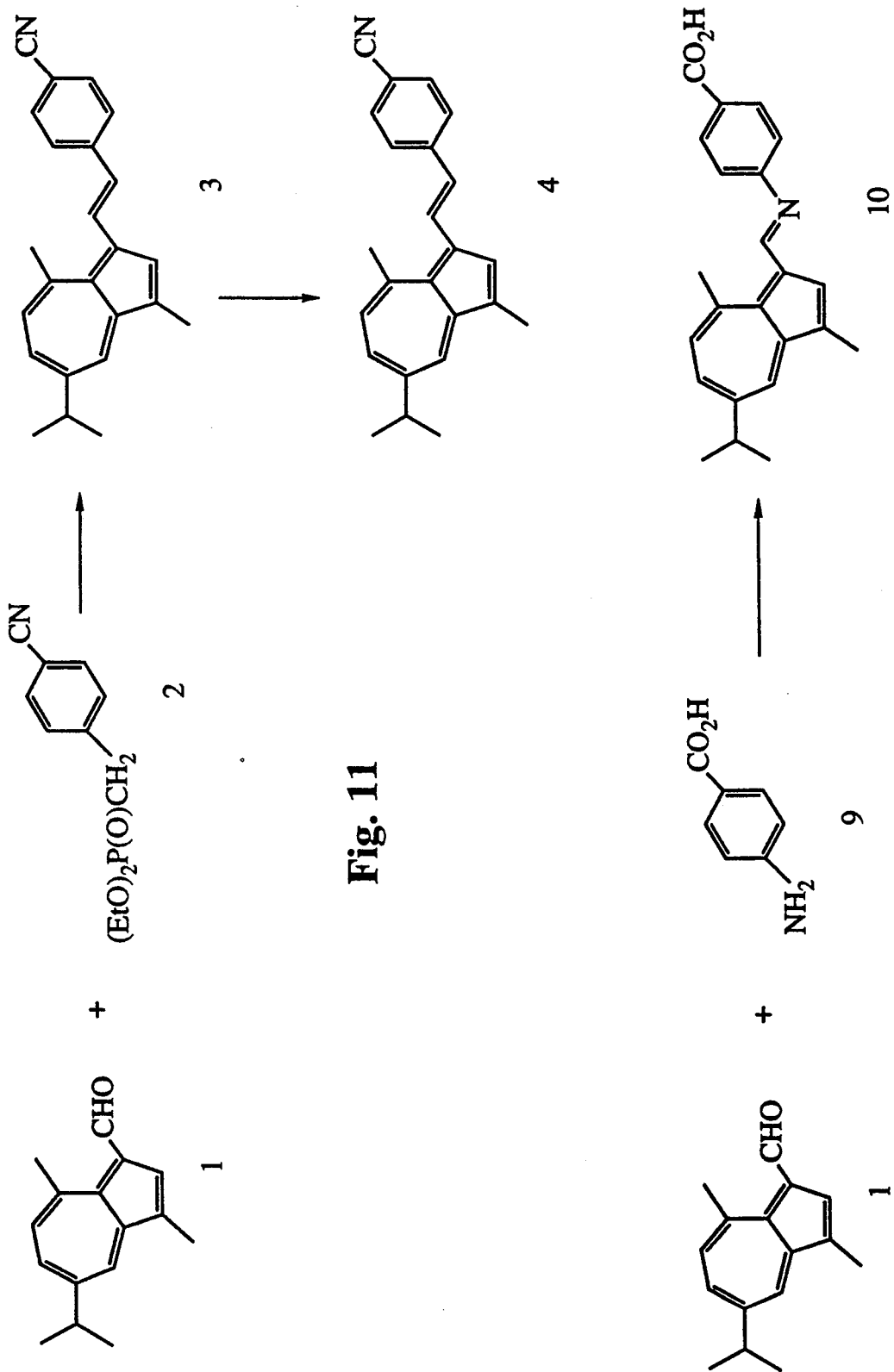

The azulenic retinoid compound of the invention identified by the formula:

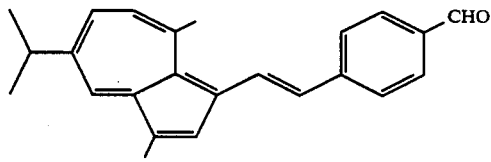

is prepared from guaiazulene-1-carboxaldehyde generally as described in FIG. 11, as follows: To a stirred, cooled (−78° C.) solution of diisoprophylamine (0.2 g, 2.0 mmol) in anhydrous tetrahydrofuran (THF, 15 mL) under an argon atmosphere is added a solution of n-butyllithium (0.5 mL, 2.5M, 1.25 mmol) over 1 min. After stirring at RT for 15 min. the solution of lithium diisopropylamide (LDA) is recooled to −78° C. and a solution of diethyl (4-cyanophenyl)methylphosphonate 2 (0.3 g., 1.2 mmol) in THF (10 mL) is added via cannula over 2 min. After stirring for 30 min., a THF (10 mL) solution of guaiazulene-1-carboxaldehyde 1 (0.2 g., 0.88 mmol) is added via cannula and the final solution stirred at RT for 4 hours. At this time dilute citric acid is added and the dark organic layer separated. The aqueous layer is extracted with ether (three 10 mL portions), the combined organic layers backwashed with water (two 10 mL portions), brine (10 mL), dried (MgSO$_4$) and concentrated in vacuo to afford crude nitrile 3 as a back viscous oil. Filtration of crude 3 through a short column of silica gel using 20% ethyl acetate-hexane removes unreacted phosphonate 2.

To a stirred, cooled (−78° C.) solution of nitrile 3 in THF (15 mL) is added a solution of DIBAL, (2 mL, 1.0M in hexanes) over 1 min. After stirring for 15 min. at −78° C. followed by 1 hour at RT, the reaction mixture is quenched with an ether slurry of silica gel (10 g) containing water (1 g) (hereafter referred to as wet silica gel). After an additional hour of stirring at RT the mixture is filtered and the organic solvents removed in vacuo. Filtration of the crude aldehyde 4 through a short column of silica gel using 20% ethyl acetate in hexane affords pure 4-[2-(1-guaiazulenyl)ethenyl]benzaldehyde 4 (approximately 70 mg) as a black solid.

EXAMPLE 18

Figure 12:
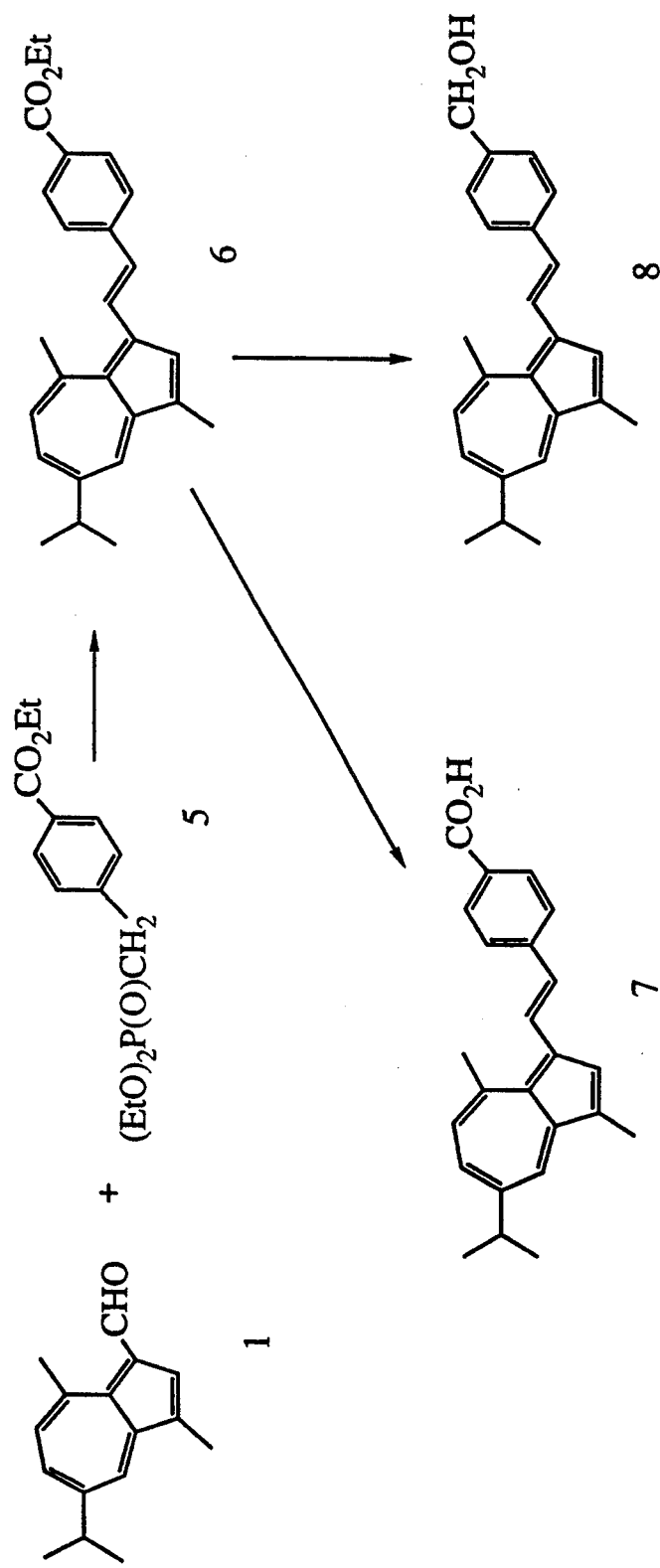
Figure 14:
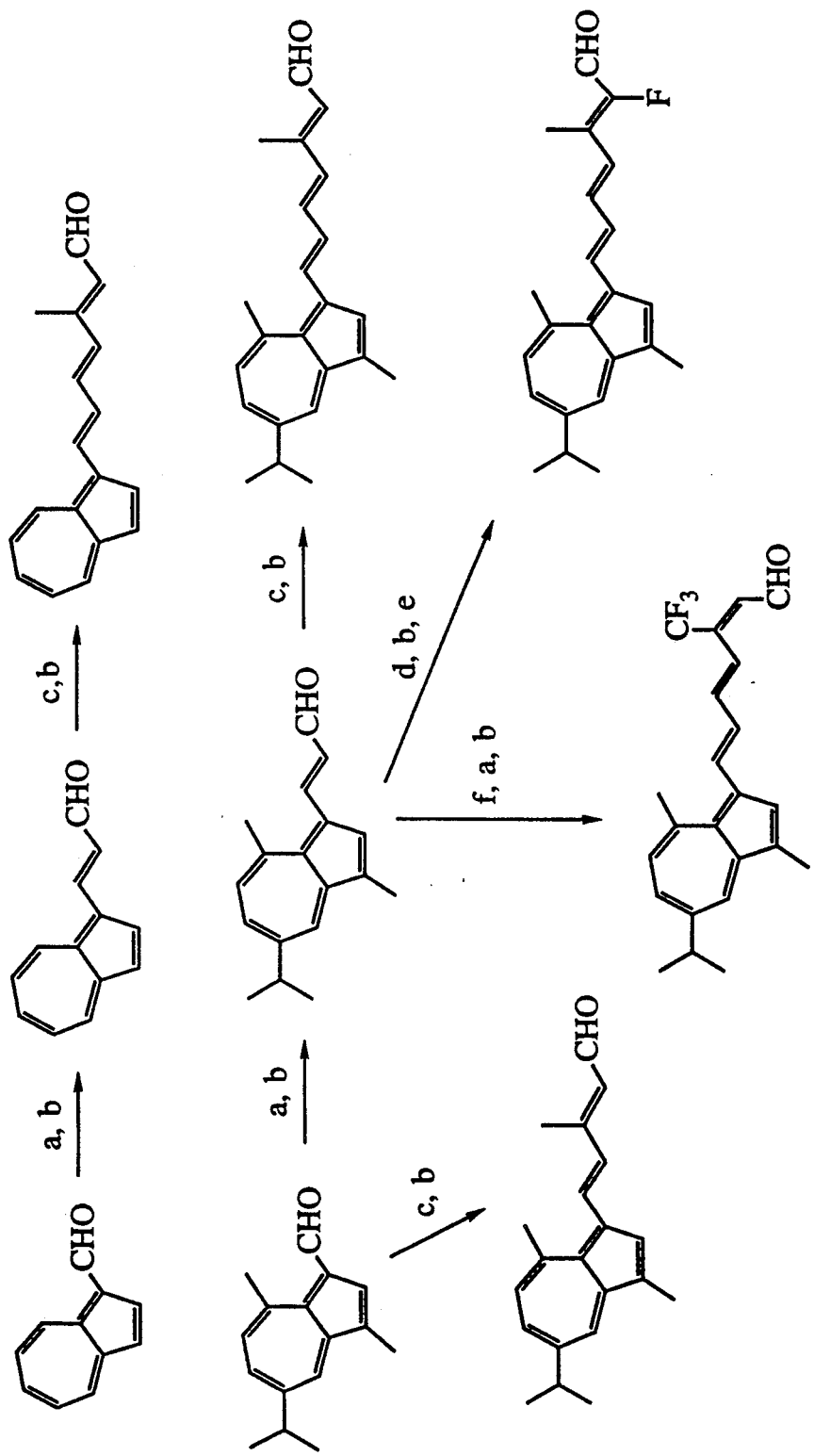
FIG. 14 is a diagrammatic representation of a "flowchart" synthetic protocol for selected azulenic retinoid compounds of the present invention.

The azulenic retinoid compound of the invention identified by the formula:

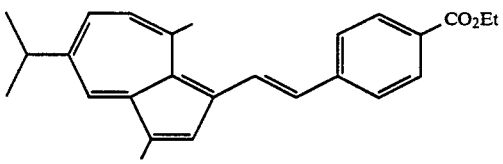

is prepared from guaiazulene-1 carboxaldehyde generally as described in FIG. 12, as follows:

Lithium diisoprophylamide (LDA) is prepared from diisopropylamine (1.62 g) and butyllithium (5.2 mL, 2.5M in hexane) in THF 10 mL). To this stirred, cooled (−78° C.) solution of LDA is added a solution of ethyl 4-[(diethoxyphosphinyl)methyl]benzoate 5 (3.72 g) in THF (10 mL) to give a deep red solution of the lithium salt. After an additional 10 min. a solution of guaiazulene-1-carboxaldehyde 1 (2.26 g) in THF (15 mL) is added and the reaction mixture stirred at RT for 2.5 hours. At this time the reaction is worked up by treatment with aqueous citric acid and extraction with ether-hexanes (1:1). The combined organic layers are sequentially washed with water and brine solution, dried (MgSO$_4$), filtered and concentrated in vacuo. The desired guaiazulenic benzoate ester 6 is obtained as a dark green solid after separation by column chromatography on silica gel using 10% ether-hexanes with added dichloromethane for improved solubility. Recrystallization from ethyl acetate-hexane affords pure ethyl 4-[2-(1-guaiazulenyl)ethenyl]benzoate 6 (1.83 g).

EXAMPLE 19

The azulenic retinoid compound of the invention identified by the formula:

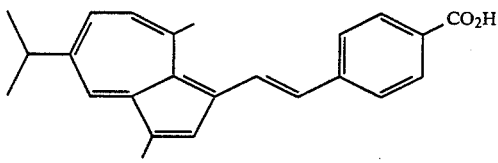

is prepared from guaiazulene-1 carboxaldehyde generally as described in FIG. 12, as follows:

Ester 6 (approximately 0.2 g) (obtained as described in Example 18) is gently refluxed with KOH (5 g) in methanol (50 mL) for three hours. After cooling, acidification, ether extraction and column chromatography using ethyl acetate, the desired azulenic benzoic acid 7 is obtained as a black solid. Recrystalization from ethyl acetate-hexane affords pure 4-[2-(1-guaiazulenyl)ethenyl]benzoic acid 7 (0.108 g).

EXAMPLE 20

The azulenic retinoid compound of the invention identified by the formula:

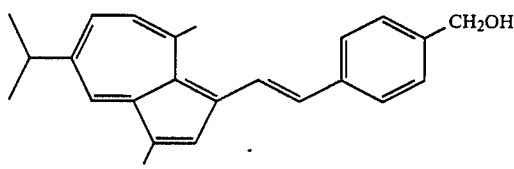

is prepared from guaiazulene-1 carboxaldehyde generally as described in FIG. 12, as follows:

Ester 6 (0.249 g) (obtained as described in Example 18) reduced in ether (20 mL) and dichloromethane (5 mL) at $-78°$ C. using an excess of DIBAL (5mL, 1M in hexane) followed by wet silica gel workup gives the desired gualazulenic benzyl alcohol 8 as a green solid. Recrystallization from ether-hexane gives pure 4[2-(1-guaiazulenyl)ethenyl]benzyl alcohol 8 (0.177 g) as an emerald green solid.

EXAMPLE 21

The azulenic retinoid compound of the invention identified by the formula:

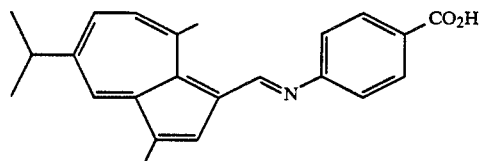

is prepared from guaiazulene-1-carboxaldehyde generally as described in FIG. 13, as follows:

A mixture of guaiazulene-1-carboxaldehyde 1 (0.179 g) and 4-aminobenzoic acid (PABA) 9 (0.11 g) is dissolved in ether (15 mL) to afford a purple solution. After standing overnight at RT, chloroform is added to precipitate unreacted 5. The brick red crude product is partially digested in boiling acetonitrile and the undissolved black residual solid filtered and washed with more acetonitirle to afford the desired guaiazulenic imino acid 10 (0.044 g). A second crop of 10 (0.045 g) is obtained from the filtrate.

Following the protocols outlined in Examples 1 through 21 and the preceding disclosure, with appropriate adjustments being made to produce the desired end product, one will be able to obtain additional azulenic retinoid compounds of the present invention.

In order to demonstrate the utility and efficacy of compounds and compositions in accordance with the present invention, the following examples illustrate certain embodiments thereof.

EXAMPLE 22

A therapeutic composition of the invention adapted for oral administration as a capsule can be prepared from the present azulenic retinoid compounds, as follows:

| Ingredient | Per Capsule |
|---|---|
| Compound of Examples 1 through 21 | 0.1 mg |
| wax mixture | 50.5 mg |
| vegetable oil | 98.9 mg |
| ethylenediaminetetraacetic acid trisodium salt | 0.5 mg |

EXAMPLE 23

A therapeutic composition of the invention adapted for topical administration as a salve can be prepared from the present azulenic retinoid compounds, as follows:

| Ingredient | Percentage |
|---|---|
| Compound of Examples 1 through 21 | 0.1 |
| vaseline white | 35 |
| wax white | 10 |
| paraffin oil viscous | 18 |
| DEHYMULSE E | 7 |
| benzoic acid USP | 0.2 |
| water deionized | add 100 |

*high molecular weight aliphatic mixed ester (supplied by Henkel)

EXAMPLE 24

The use of the azulenic retinoid compounds prepared in accordance with Examples 1-21 as anti-neoplasm agents is demonstrated by their ability to inhibit the proliferation of carcinoma cells.

The KB assay has been established by the U.S. National Cancer Institute (Geran, et al., *Cancer Chemother. Rep.* 3:1-103 (1972) and is widely used to evaluate the cytotoxicity of plant extracts.

Human epidermoid carcinoma (KB) cells (ATCC accession number CCL 17) are seeded at an initial cell density of $10^5$ cells into a 6 cm dish (Costar) containing 5 mL of Eagle's basal medium (Gibco), pH 7.25, which has been supplemented with 5% newborn calf serum (Gibco), 20 mM HEPES buffer and 50 µg/mL gentamicin sulfate (Sigma Chemical Co.).

Immediately following seeding, aliquots of the azulenic retinoid compounds at concentrations of from 0.011 to 0.041M in ethanol were added in volumes of 1–10µL/mL of cell culture medium.

The cultures were incubated for four days at 37° C. in a humidified 5% $CO_2$ atmosphere. The cytotoxicity of the subject compounds is estimated visually on the basis of cell number and morphology at periods of 48, 72, and 96 hours post-exposure.

The results of these cytotoxicity tests are reported as the Minimum Inhibitory Concentrations presented in Table 1.

TABLE 1

| Retinoid Compound | MIC Result |
|---|---|
| 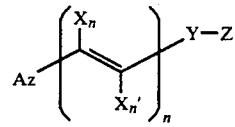 CH$_2$OH | <1 µl/mL |
| 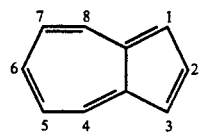 CO$_2$Me | >10 µl/mL |
| (structure) CO$_2$H | >10 µl/mL |
| (structure) CHO | 0.01 µl/mL |
| 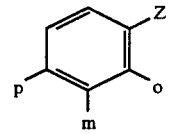 CHO, F | 1 µl/mL |

Thus it can be seen that the present azulenic retinoid compounds provide novel and improved compounds, compositions and methods for their use as anti-cancer and cancer-prevention agents. The compositions of the present invention will also find use in treating dermatological disorders such as acne and psoriasis, as well as dermatologically-related conditions such as repair and effacement of wrinkles.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

We claim:

1. An azulenic retinoid compound having anti-neoplasm, and/or anti-dermatopathic activity in mammals, which comprises a compound in accordance with the formula:

$$Az \left( \begin{matrix} X_n \\ X_{n'} \end{matrix} \right)_n Y-Z$$

Wherein
n is an integer from 1 to 4;
each $X_n$ or $X_{n'}$ group can independently be taken to be H, alkyl, F, Cl or CF$_3$;
Az is an azulenic substituent group of the following general formula:

(azulene structure with positions 1-8)

wherein
the azulenic group is attached via any of carbons 1 to 8 to the unsaturated retinoid backbone, and
the azulene group can be further modified by additional alkyl substituents at any one or more of the remaining carbons;
the Y group is C$_{1-10}$ straight or branched chain alkyl or an aromatic functional group of the following formula:

(benzene ring with p, m, o, Z positions)

wherein the Y group is bonded to the unsaturated retinoid backbone at either the para- (p), meta- (m), or ortho- (o)-position of the benzene ring, or is des-Y; and
the Z group is any polar end group;
with the provisos that:
when the Az group is azulene attached to the unsaturated retinoid backbone via the 1' carbon or guaiazulene attached to the unsaturated retinoid backbone via the 3' carbon, and n=1 or 2, then at least one of the following limitations apply:
at least one $X_n$ or $X_{n'}$ group is not H;
Y is not des-Y; or
z is not CHO;
when the Az group is azulene attached to the unsaturated retinoid backbone via the 2' carbon, then at least one of the following limitations apply:
when n=1, then either X$_1$ is not CH$_3$ or Y is not des-Y, or Z is not CHO; or
when n=3, then either X$_3$ is not CH$_3$ or Y is not des-Y, or Z is not CHO or COOCH$_3$CH$_2$OH.

2. The compound of claim 1 which is

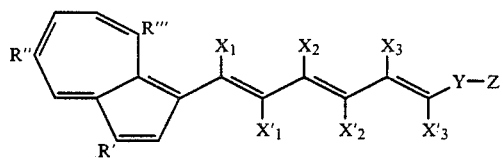

wherein
each $X_n$ and $X_n'$ group is independently taken to be H, $C_{1-3}$ alkyl, F, Cl or $CF_3$;
Y is des-Y;
R; R' and R''' are independently taken to be H or $C_{1-3}$ alkyl; and
the Z group is any polar end group.

3. A composition useful as an anti-neoplasm and/or anti-dermatopathic agent comprising a therapeutically effective amount of at least one azulenic retinoid compound having anti-neoplasm, and/or anti-dermatopathic activity in mammals, which comprises a compound in accordance with the formula:

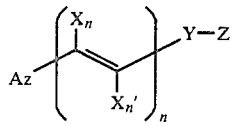

Wherein
n is an integer from 1 to 4;
each $X_n$ or $X_n'$ group is independently taken to be H, alkyl, F, Cl or $CF_3$;
Az is an azulenic substituent group of the following general formula:

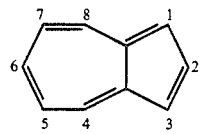

wherein
the azulenic group is attached via any of carbons 1 to 8 to the unsaturated retinoid backbone, and
the azulene group can be further modified by additional alkyl substituents at any one or more of the remaining carbons;
the Y group is $C_{1-10}$ straight or branched chain alkyl or an aromatic functional group of the following formula:

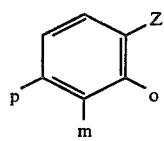

wherein the Y group is bonded to the unsaturated retinoid backbone at either the para- (p), meta- (m), or ortho- (o)-position of the benzene ring, or is des-Y; and
the Z group is any polar end group; together with a pharmaceutically acceptable carrier.

4. A method for preventing or treating carcinomas or dermatopathic conditions in a mammalian host, which comprises administering to said host a pharmaceutically effective amount of the composition of claim 3.

5. The compound of claim 2 wherein
each R group is independently selected from the group consisting of H, $CH_3$ and $CH(CH_3)_2$.

6. The compound of claim 2 wherein Z is a polar group selected from the group consisting of CHO, $CH_2OH$, $CH_2OCOCH_3$, $CO_2H$, $CO_2R$, and CONRR', where R and R' are each independently selected from the group consisting of H and $C_{1-3}$ alkyl groups.

7. The compound of claim 1 which is selected from the group consisting of:

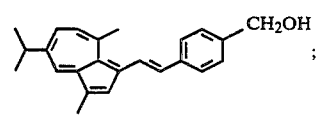

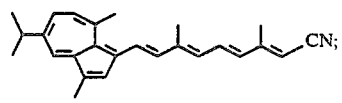

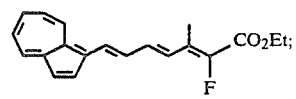

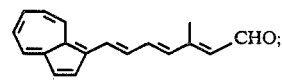

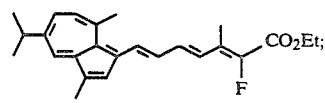

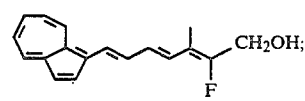

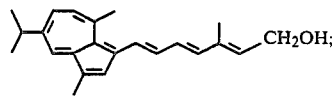

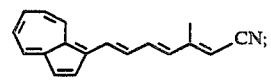

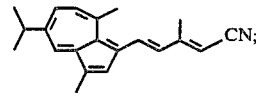

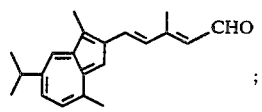

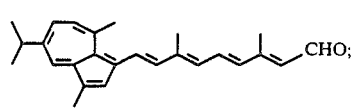

-continued

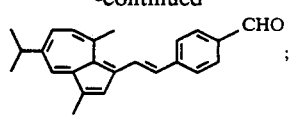
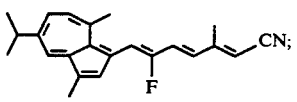
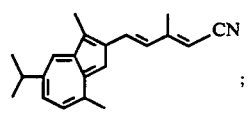
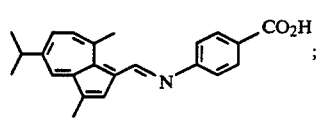
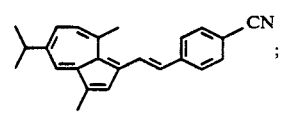
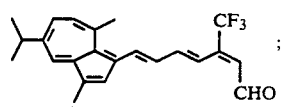
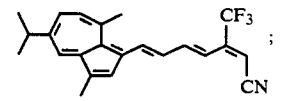
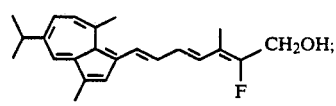
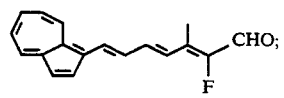
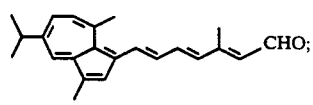
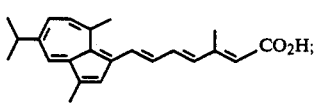
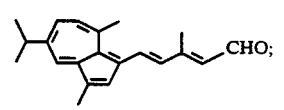
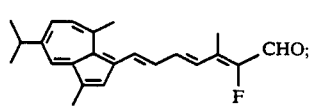

-continued

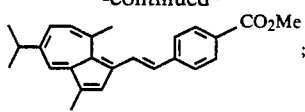
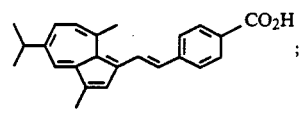
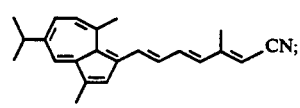
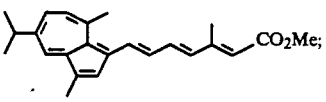
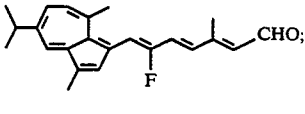
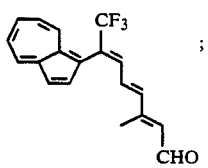
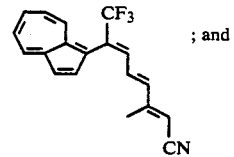
; and
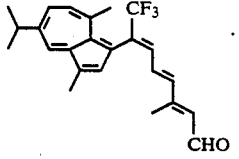

8. The composition of claim 3 wherein each R group is independently selected from the group consisting of H, H$_3$ and CH(CH$_3$)$_2$.

9. The composition of claim 3 wherein Z is a polar group selected from the group consisting of CHO, CH$_2$OH, CH$_2$OCOCH$_3$, CO$_2$H, CO$_2$R, and CONRR', where R and R' are each independently selected from the group consisting of H and C$_{1-3}$ alkyl groups.

10. The composition of claim 3 comprising a compound which is selected from the group consisting of:

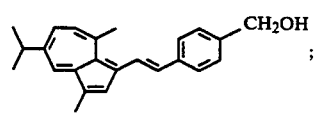
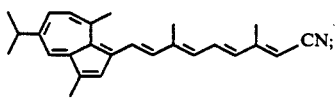

-continued

-continued
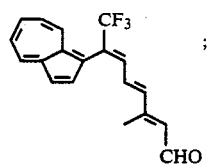
-continued
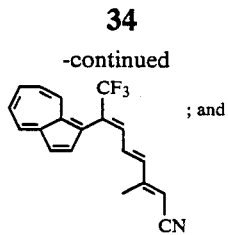
; and
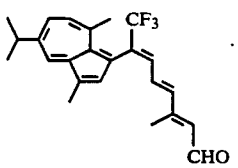
* * * * *